(12) United States Patent
McCarty et al.

(10) Patent No.: US 8,106,013 B2
(45) Date of Patent: Jan. 31, 2012

(54) ABC TRANSPORTER LIGAND GATX1

(75) Inventors: Nael McCarty, Atlanta, GA (US);
Matthew Fuller, Social Circle, GA (US); Julia Kubanek, Decatur, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 12/299,881

(22) PCT Filed: May 18, 2007

(86) PCT No.: PCT/US2007/069243
§ 371 (c)(1),
(2), (4) Date: Nov. 6, 2008

(87) PCT Pub. No.: WO2007/137163
PCT Pub. Date: Nov. 29, 2007

(65) Prior Publication Data
US 2009/0203598 A1    Aug. 13, 2009

Related U.S. Application Data

(60) Provisional application No. 60/801,863, filed on May 19, 2006.

(51) Int. Cl.
*A61K 38/16* (2006.01)
*C07K 14/435* (2006.01)
*A61P 1/12* (2006.01)
*A61P 13/12* (2006.01)

(52) U.S. Cl. ............ 514/17.4; 514/15.4; 514/21.3; 514/867; 530/324; 530/855

(58) Field of Classification Search ............... None
See application file for complete search history.

(56) References Cited

U.S. PATENT DOCUMENTS

| | | | |
|---|---|---|---|
| 4,272,398 A | 6/1981 | Jaffe | |
| 4,683,195 A | 7/1987 | Mullis et al. | |
| 4,683,202 A | 7/1987 | Mullis | |
| 4,861,627 A | 8/1989 | Mathiowitz et al. | |
| 4,925,673 A | 5/1990 | Steiner et al. | |
| 5,013,556 A | 5/1991 | Woodle et al. | |
| 5,223,409 A | 6/1993 | Ladner et al. | |
| 5,284,656 A | 2/1994 | Platz et al. | |
| 5,288,707 A | 2/1994 | Metternich | |

(Continued)

FOREIGN PATENT DOCUMENTS

EP    0 374 753    6/1990

(Continued)

OTHER PUBLICATIONS

Wells (1990) Biochemistry 29(37): 8509-8517.*

(Continued)

*Primary Examiner* — Bridget E Bunner
*Assistant Examiner* — Zachary Howard
(74) *Attorney, Agent, or Firm* — Pabat Patent Group LLP

(57) ABSTRACT

Compositions and methods of using scorpion venom peptide that is a ligand for ABC transporters. One aspect provides a peptide having at least 80% sequence identity to SEQ ID NO: 1. The peptide Is believed to have a molecular mass of about 3.7 kDa and specifically interacts with cystic fibrosis transmembrane conductance regulator. Methods of treating a disorder or symptom of a disorder related to aberrant ABC transporter activity are also provided.

10 Claims, 10 Drawing Sheets

U.S. PATENT DOCUMENTS

| | | | |
|---|---|---|---|
| 5,451,569 | A | 9/1995 | Wong et al. |
| 5,494,895 | A | 2/1996 | Garcia et al. |
| 5,552,534 | A | 9/1996 | Hirschmann et al. |
| 5,707,829 | A | 1/1998 | Jacobs et al. |
| 5,811,515 | A | 9/1998 | Grubbs et al. |
| 5,817,626 | A | 10/1998 | Findeis et al. |
| 5,817,879 | A | 10/1998 | Hirschmann et al. |
| 5,821,231 | A | 10/1998 | Arrhenius et al. |
| 5,874,529 | A | 2/1999 | Gilon et al. |
| 6,593,141 | B1 | 7/2003 | Herman et al. |
| 6,689,749 | B1 | 2/2004 | Lebrun et al. |
| 6,768,002 | B1 | 7/2004 | Herrmann et al. |
| 2005/0042717 | A1 | 2/2005 | Herrmann et al. |
| 2006/0014928 | A1 | 1/2006 | Perez-Garcia et al. |
| 2006/0088899 | A1* | 4/2006 | Alvarez et al. ............... 435/12 |

FOREIGN PATENT DOCUMENTS

| | | |
|---|---|---|
| WO | WO 9004036 | 4/1990 |
| WO | WO 9010077 | 9/1990 |
| WO | WO 9206204 | 4/1992 |
| WO | WO 9216637 | 10/1992 |
| WO | WO 9428114 | 12/1994 |
| WO | WO 9503065 | 2/1995 |
| WO | WO 9506764 | 3/1995 |
| WO | WO 9523225 | 8/1995 |
| WO | WO 9636221 | 11/1996 |
| WO | WO 9636712 | 11/1996 |
| WO | WO 9720078 | 6/1997 |
| WO | WO 9829446 | 7/1998 |
| WO | WO 0024772 | 5/2000 |
| WO | WO 0032777 | 6/2000 |
| WO | WO 03101475 A1 | 12/2003 |
| WO | WO 2004056314 | 7/2004 |

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only. Bork (2000) Genome Research 10:398.*

Bork (2000) Genome Research 10:398.*

Skolnick et al (2000) Trends in Biotech. 18(1): 34.*

Doerks et al (1998) Trends in Genetics 14(6): 248.*

Brenner (1999) Trends in Genetics 15(4): 132.*

Buisine et al, 1997. J. Peptide Res. 49: 545-555.*

Thompson et al, 2009. The Journal of Biological Chemistry. 284(38): 26051-26062.*

Shen et al (2005. Journal of Neuro-Oncology. 71: 113-119).*

Thiagarajah et al, 2004. The FASEB Journal. pp. 1-15.*

Li et al, 2010. Integr Biol 2(4): 161-177.*

Al-Awqati, et al., "Alternative treatment for secretory diarrhea revealed in a new class of CFTR inhibitors", *J Clin. Invest.*, 110(11):1599-601(2002).

Al-Nakkash and Hwang, "Activation of wild-type and deltaF508-CFTR by phosphodiesterase inhibitors through cAMP-dependent and -independent mechanisms", *Pflugers Arch.*, 437(4):553-61 (1999).

Bowie and Sauer, "Identifying determinants of folding and activity for a protein of unknown structure", *Proc. Natl. Acad. Sci. USA*, 86(7):2152-6 (1989).

Castle, et al., "Toxins in the characterization of potassium channels", *TINS*, 12:59-65 (1989).

Chang, et al., "Predominant interactions between μ-conotoxin Arg-13 and the skeletal muscle Na+ channel localized by mutant cycle analysis", *Biochemistry* 37: 4407-4419 (1998).

Cornish-Bowden, et al., "Nomenclature for incompletely specified bases in nucleic acid sequences: recommendations 1984.", *Nucleic Acids Res.*, 13(9):3021-30 (1985).

Csanady, et al., "Served channels probe regulation of gating of cystic fibrosis transmembrane conductance regulator by its cytoplasmic domains", *J. Gen. Physiol.*, 116:477-500 (2000).

Dalton, et al., "Chlorotoxin-sensitive Ca2+ -activated Cl- channel in type R2 reactive astrocytes from adult rat brain", *Glia*, 42:325-339 (2003).

Debin and Strichartz, "Chloride channel inhibition by the venom of the scorpion Leiurus quinquestriatus", *Toxicon*, 29(11):1403-8 (1991).

Debin, et al., "Purification and characterization of chlorotoxin, a chloride channel ligand from the venom of the scorpion", *Am. J. Physiol.*, 264(2 Pt 1):C361-9 (1993).

Deshane, et al., "Chlorotoxin inhibits glioma cell invasion via matrix metalloproteinase-2", *J. Biol. Chem.*, 278, 4135-4144 (2003).

Elble and Pauli, "Tumor suppression by a proapoptotic calcium-activated chloride channel in mammary epithelium", *J. Biol. Chem.*, 276(44):40510-7 (2001).

Estève, et al., "Transduction of the scorpion toxin maurocalcine into cells", *J. Biol. Chem.* 280:12833-12839 (2005).

Froy, et al., "Dynamic diversification from a putative common ancestor of scorpion toxins affecting sodium, potassium, and chloride channels", *J. Mol. Evol.*, 48:187-196 (1999).

Fu, et al., "Therapeutic potential of chlorotoxin-like neurotoxin from the Chinese scorpion for human gliomas", *Neurosci. Lett.*, 412(1):62-7 (2007).

Fuller, et al., "Inhibition of CFTR channels by a peptide toxin of scorpion venom", *Am. J. Physiol. Cell. Physiol.*, 287(5):C1328-41 (2004).

Fuller, et al., "The block of CFTR by scorpion venom is state-dependent", *Biophys. J.*, 89:3960-3975 (2005).

Fuller, et al. "State-dependent inhibition of cystic fibrosis transmembrane conductance regulator chloride channels by a novel peptide toxin", *J. Biol. Chem.*, 282(52):37545-55 (2007).

Gadsby, et al., "The ABC protein turned chloride channel whose failure causes cystic fibrosis", *Nature*, 440:477-483 (2006).

Gerard, et al., "Alterations of ionic membrane permeabilities in multidrug-resistant neuroblastoma x glioma hybrid cells", *J. Exp. Biol.*, 201(Pt 1):21-31 (1998).

Gimenez-Gallego, et al., "Purification, sequence, and model structure of charybdotoxin, a potent selective inhibitor of calcium-activated potassium channels", *Proc. Natl. Acad. Sci. USA*, 85:3329-3333 (1988).

Goldstein and Miller, "A point mutation in a Shaker K+ channel changes its charybdotoxin binding site from low to high affinity", *Biophys. J.*, 62:5-7 (1992).

Gottlieb and Dosanjh, "Mutant cystic fibrosis transmembrane conductance regulator inhibits acidification and apoptosis in C127 cells: possible relevance to cystic fibrosis", *Proc. Natl. Acad. Sci. USA*, 93(8):3587-91 (1996).

Gruber and Pauli, "Tumorigenicity of human breast cancer is associated with loss of the Ca2+-activated chloride channel CLCA2", *Cancer Res.*, 59(21):5488-91 (1999).

Grunder, et al., "Regions involved in the opening of ClC-2 chloride channel by voltage and cell volume", *Nature London*, 360:759-762 (1992).

Hanaoka and Guggino, "cAMP regulates cell proliferation and cyst formation in autosomal polycystic kidney disease cells", *J. Am. Soc. Nephrol.*, 11(7):1179-87 (2000).

Hille, "Table of Contents," *Ion Channels of Excitable Membranes*, Sunderland, MA: Sinauer Associates, Inc. (2001).

Hille, "Chaper 5: Potassium Channels and Chloride Channels," *Ion Channels of Excitable Membranes*, pp. 131-67, Sunderland, MA: Sinauer Associates, Inc. (2001).

Inoue and Okada, "Roles of volume-sensitive chloride channel in excitotoxic neuronal injury", J. Neurosci., 27(6):1445-55 (2007).

IUPAC-IUB JCBN, "IUPAC-IUB Joint Commission on Biochemical Nomenclature (JCBN). Nomenclature and symbolism for amino acids and peptides. Recommendations 1983.", *Biochem J.* 219(2):345-73 (1984).

Jiang, et al., "Suppression of cell proliferation with induction of p21 by Cl(-) channel blockers in human leukemic cells", *Eur. J. Pharmacol.*, 488(1-3):27-34 (2004).

Kayed, et al., "FXYD3 is overexpressed in pancreatic ductal adenocarcinoma and influences pancreatic cancer cell growth", *Int. J. Cancer.*, 118(1):43-54 (2006).

Kim, et al., "Role of Ca2+-activated Cl channels in the mechanism of apoptosis induced by cyclosporin A in a human hepatoma cell line", *Biochem. Biophys. Res. Commun.*, 309(2):291-7 (2003).

Klausen, et al., "Cell cycle-dependent activity of the volume- and Ca2+-activated anion currents in Ehrlich lettre ascites cells", *J. Cell Physiol.*, 210(3):831-42 (2007).

Lewis and Garcia, "Therapeutic potential of venom peptides", *Nat. Rev. Drug Discov.*, 2:1-13 (2003).

Li, et al., "The relationship between cell proliferation, Cl- secretion, and renal cyst growth: a study using CFTR inhibitors", *Kidney Int.* 66(5):1926-38 (2004).

Lippens, et al., "NMR sequential assignments and solution structure of chlorotoxin, a small scorpion toxin that blocks chloride channels", *Biochemistry* 34:13-21 (1995).

Lopatin, et al., "Novel tools for localizing ion channels in living cells", *Trends Pharmacol. Sci.*, 19(10):395-8 (1998).

Lyons, et al., "Chlorotoxin, a scorpion-derived peptide, specifically binds to gliomas and tumors of neuroectodermal origin", *Glia* 39:162-173 (2002).

Ma, et al., "Thiazolidinone CFTR inhibitor identified by high-throughput screening blocks cholera toxin-induced intestinal fluid secretion", *J. Clin. Invest.*, 110:1651-1658 (2002).

Maertens, et al., "Chlorotoxin does not inhibit volume-regulated, calcium-activated and cyclic AMP-activated chloride channels", *Br. J. Pharmacol.*, 129:791-801 (2000).

Mccarty and O'Neil, "Calcium signaling in cell volume regulation", *Physiol. Rev.*, 72: 1037-1061 (1992).

Mccarty, "Permeation through the CFTR chloride channel", *J. Exp. Biol.*, 203, 1947-1962 (2000).

Mccarty, et al., "Voltage-dependent block of the cystic fibrosis transmembrane conductance regulator Cl-channel by two closely related arylaminobenzoates", *J. Gen. Physiol.*, 102:1-23 (1993).

Newmark, et al., "Preparation and properties of adducts of streptokinase and streptokinase-plasmin complex with polyethylene glycol and pluronic polyol F38", *J. Appl. Biochem.*, 4: 185-189 (1982).

Olsen, et al., Expression of voltage-gated chloride channels in human glioma cells, *J. Neurosci.*, 23(13):5572-82 (2003).

Pappas and Ritchie, "Effect of specific ion channel blockers on cultured Schwann cell proliferation", *Glia*, 22(2):113-20 (1998).

Phipps, et al., "Chloride-channel block inhibits T lymphocyte activation and signaling", *Cell Signal.*, 8(2):141-9 (1996).

Possani, et al., "Peptides and genes coding for scorpion toxins that affect ion-channels", *Biochimie*, 82:861-868 (2000).

Ransom, et al., "Volume-activated chloride currents contribute to the resting conductance and invasive migration of human glioma cells", *J. Neurosci.*, 21(19):7674-83 (2001).

Renaudo, et al., "Cancer cell cycle modulated by a functional coupling between sigma-1 receptors and Cl-channels", *J. Biol. Chem.*, 282(4):2259-67 (2007). Epub Nov. 22, 2006.

Rouzaire-Dubois, et al., "Control of cell proliferation by cell volume alterations in rat C6 glioma cells", *Pflugers Arch.*, 440(6):881-8 (2000).

Schlichter, et al., "Properties of K+ and Cl- channels and their involvement in proliferation of rat microglial cells", *Glia*, 17(3):225-36 (1996).

Schmitt and Schmidt, "Influence of calcium ions on the ionic currents of nodes of Ranvier treated with scorpion venom", *Pflugers. Arch.* 333(1):51-61 (1972).

Schultz, et al., "Pharmacology of CFTR chloride channel activity", *Physiol. Rev.*, 79:S109-S144 (1999).

Shen, et al., "A novel function of BCL-2 overexpression in regulatory volume decrease. Enhancing swelling-activated $Ca(2^+)$ entry and $Cl(^-)$ channel activity", *J. Biol. Chem.*, 277(18):15592-9 (2002).

Shen, et al., "Differential expression of volume-regulated anion channels during cell cycle progression of human cervical cancer cells", *J. Physiol.*, 529 Pt 2:385-94 (2000).

Soroceanu, et al., "Modulation of glioma cell migration and invasion using Cl(-) and K(+) ion channel blockers", *J. Neurosci.*, 19(14):5942-54 (1999).

Szabò, et al., "Tyrosine kinase-dependent activation of a chloride channel in CD95-induced apoptosis in T lymphocytes", *Proc. Natl. Acad Sci. USA*, 95(11):6169-74 (1998).

Taddei, et al., "Altered channel gating mechanism for CFTR inhibition by a high-affinity thiazolidinone blocker", *FEBS Lett.*, 558, 52-56 (2004).

Thompson, et al., "Inhibition of ClC-2 Cl- channels by a peptide component of scorpion venom", *J. Membr. Biol.*, 208:65-76 (2005).

Wondergem, et al., "Blocking swelling-activated chloride current inhibits mouse liver cell proliferation", *J. Physiol.*, 532(Pt 3):661-72 (2001).

Yang, et al., "siRNA-mediated silencing of ClC-2 gene inhibits proliferation of human U-87 glioma cells", *Ai Zheng.*, 25(7):805-10 (2006). (with English abstract).

Zeng, et al., "Cloning and characterization of a cDNA sequence encoding the precursor of a chlorotoxin-like peptide from the Chinese scorpion Buthus martensii Karsch", *Toxicon*, 38(8):1009-14 (2000).

Zhang, et al., "Direct comparison of NPPB and DPC as probes of CFTR expressed in Xenopus oocytes", *J. Membr. Biol.*, 175:35-52 (2000).

Zhang, et al., "Steady-state interactions of glibenclamide with CFTR: evidence for multiple sites", *J. Membr. Biol.*, 199:15-28 (2004).

Adjadj, et al., "Solution structure of Lqh-8/6, a toxin-like peptide from a scorpion venom-structural heterogeneity induced by prolinc cis/trans isomerization," *Eur. J. Biochem.*, 246(1):218-27 (1997).

\* cited by examiner

SEQUENCE LISTING

```
<160> NUMBER OF SEQ ID NOS: 39

<210> SEQ ID NO 1
<211> LENGTH: 34
<212> TYPE: PRT
<213> ORGANISM: Leiurus quinquestriatus hebraeus

<400> SEQUENCE: 1

Cys Gly Pro Cys Phe Thr Thr Asp His Gln Met Glu Gln Lys Cys Ala
1               5                   10                  15

Glu Cys Cys Gly Gly Ile Gly Lys Cys Tyr Gly Pro Gln Cys Leu Cys
            20                  25                  30

Asn Arg

<210> SEQ ID NO 2
<211> LENGTH: 102
<212> TYPE: DNA
```

-continued

<213> ORGANISM: Leiurus quinquestriatus hebraeus

<400> SEQUENCE: 2
tgtggacctt gctttacaac ggatcatcaa atggaacaga agtgtgcaga atgttgcgga 60
ggcattggaa aatgctatgg tccacaatgt ttgtgtaata gg 102

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg Arg
1 5 10

<210> SEQ ID NO 4
<211> LENGTH: 9
<212> TYPE: PRT
<213> ORGANISM: artificial sequence
<220> FEATURE:
<223> OTHER INFORMATION: synthetic protein transduction domain

<400> SEQUENCE: 4

Arg Lys Lys Arg Arg Gln Arg Arg Arg
1 5

<210> SEQ ID NO 5
<211> LENGTH: 15
<212> TYPE: RNA
<213> ORGANISM: artificial sequenec
<220> FEATURE:
<223> OTHER INFORMATION: synthetic siRNA

<400> SEQUENCE: 5
ggaggcauug gaaaa 15

<210> SEQ ID NO 6
<211> LENGTH: 14
<212> TYPE: RNA
<213> ORGANISM: artificial sequence
<220> FEATURE:
<223> OTHER INFORMATION: synthetic siRNA

<400> SEQUENCE: 6
uggaccuugc uuua 14

<210> SEQ ID NO 7
<211> LENGTH: 15
<212> TYPE: RNA
<213> ORGANISM: artificial sequence
<220> FEATURE:
<223> OTHER INFORMATION: synthetic siRNA

<400> SEQUENCE: 7
ggaccuugcu uuaca 15

<210> SEQ ID NO 8
<211> LENGTH: 15
<212> TYPE: RNA
<213> ORGANISM: artificial sequence
<220> FEATURE:
<223> OTHER INFORMATION: synthetic siRNA

<400> SEQUENCE: 8
acaacggauc aucaa 15

```
<210> SEQ ID NO 9
<211> LENGTH: 14
<212> TYPE: RNA
<213> ORGANISM: artificial sequensce
<220> FEATURE:
<223> OTHER INFORMATION: synthetic siRNA

<400> SEQUENCE: 9
cagaagugug caga                                                        14

<210> SEQ ID NO 10
<211> LENGTH: 14
<212> TYPE: RNA
<213> ORGANISM: artificial sequence
<220> FEATURE:
<223> OTHER INFORMATION: synthetic siRNA

<400> SEQUENCE: 10
caauguuugu guaa                                                        14

<210> SEQ ID NO 11
<211> LENGTH: 15
<212> TYPE: RNA
<213> ORGANISM: artificial sequence
<220> FEATURE:
<223> OTHER INFORMATION: synthetic siRNA

<400> SEQUENCE: 11
caauguuugu guaau                                                       15

<210> SEQ ID NO 12
<211> LENGTH: 14
<212> TYPE: RNA
<213> ORGANISM: artificial sequence
<220> FEATURE:
<223> OTHER INFORMATION: synthetic siRNA

<400> SEQUENCE: 12
acaacggauc auca                                                        14

<210> SEQ ID NO 13
<211> LENGTH: 15
<212> TYPE: RNA
<213> ORGANISM: artificial sequence
<220> FEATURE:
<223> OTHER INFORMATION: synthetic siRNA

<400> SEQUENCE: 13
gaacagaagu gugca                                                       15

<210> SEQ ID NO 14
<211> LENGTH: 14
<212> TYPE: RNA
<213> ORGANISM: artificial sequence
<220> FEATURE:
<223> OTHER INFORMATION: synthetic siRNA

<400> SEQUENCE: 14
gaagugugca gaau                                                        14

<210> SEQ ID NO 15
<211> LENGTH: 14
<212> TYPE: RNA
<213> ORGANISM: artificial sequence
<220> FEATURE:
<223> OTHER INFORMATION: synthetic siRNA
```

-continued

```
<400> SEQUENCE: 15
ggaggcauug gaaa                                                         14

<210> SEQ ID NO 16
<211> LENGTH: 15
<212> TYPE: RNA
<213> ORGANISM: artificial seqence
<220> FEATURE:
<223> OTHER INFORMATION: synthetic siRNA

<400> SEQUENCE: 16
ugcuaugguc cacaa                                                        15

<210> SEQ ID NO 17
<211> LENGTH: 14
<212> TYPE: RNA
<213> ORGANISM: artificial sequence
<220> FEATURE:
<223> OTHER INFORMATION: synthetic siRNA

<400> SEQUENCE: 17
aacggaucau caaa                                                         14

<210> SEQ ID NO 18
<211> LENGTH: 19
<212> TYPE: PRT
<213> ORGANISM: Drosophila melanogaster

<400> SEQUENCE: 18

Ser Gly Arg Gln Ile Lys Ile Trp Phe Gln Asn Arg Arg Met Lys Trp
1               5                   10                  15

Lys Lys Cys

<210> SEQ ID NO 19
<211> LENGTH: 14
<212> TYPE: PRT
<213> ORGANISM: Drosophila melanogaster

<400> SEQUENCE: 19

Ser Gly Tyr Gly Arg Lys Lys Arg Arg Gln Arg Arg Arg Cys
1               5                   10

<210> SEQ ID NO 20
<211> LENGTH: 34
<212> TYPE: PRT
<213> ORGANISM: Leiurus quinquestriatus hebraeus

<400> SEQUENCE: 20

Cys Gly Pro Cys Phe Thr Thr Asp His Gln Thr Glu Gln Lys Cys Ala
1               5                   10                  15

Glu Cys Cys Gly Gly Ile Gly Lys Cys Tyr Gly Pro Gln Cys Leu Cys
                20                  25                  30

Asn Arg

<210> SEQ ID NO 21
<211> LENGTH: 33
<212> TYPE: PRT
<213> ORGANISM: Leiurus quinquestriatus hebraeus

<400> SEQUENCE: 21

Cys Gly Pro Cys Phe Thr Thr Asp His Gln Thr Glu Gln Lys Cys Ala
1               5                   10                  15

Glu Cys Cys Gly Gly Ile Gly Lys Cys Tyr Gly Pro Gln Cys Leu Cys
```

```
                 20                  25                  30

Arg

<210> SEQ ID NO 22
<211> LENGTH: 33
<212> TYPE: PRT
<213> ORGANISM: Leiurus quinquestriatus hebraeus

<400> SEQUENCE: 22

Cys Gly Pro Cys Phe Thr Thr Asp Arg Gln Met Glu Gln Lys Cys Ala
1               5                  10                  15

Glu Cys Cys Gly Gly Ile Gly Lys Cys Tyr Gly Pro Gln Cys Leu Cys
            20                  25                  30

Arg

<210> SEQ ID NO 23
<211> LENGTH: 35
<212> TYPE: PRT
<213> ORGANISM: Mesobuthus martensii

<400> SEQUENCE: 23

Cys Gly Pro Cys Phe Thr Thr Asp Ala Asn Met Ala Arg Lys Cys Arg
1               5                  10                  15

Glu Cys Cys Gly Gly Ile Gly Lys Cys Phe Gly Pro Gln Cys Leu Cys
            20                  25                  30

Asn Arg Ile
        35

<210> SEQ ID NO 24
<211> LENGTH: 35
<212> TYPE: PRT
<213> ORGANISM: Mesobuthus martensii

<400> SEQUENCE: 24

Cys Gly Pro Cys Phe Thr Thr Asp Ala Asn Met Ala Arg Lys Cys Arg
1               5                  10                  15

Glu Cys Cys Gly Gly Asn Gly Lys Cys Phe Gly Pro Gln Cys Leu Cys
            20                  25                  30

Asn Arg Glu
        35

<210> SEQ ID NO 25
<211> LENGTH: 35
<212> TYPE: PRT
<213> ORGANISM: Androctonus mauretanicus mauretanicus

<400> SEQUENCE: 25

Cys Gly Pro Cys Phe Thr Thr Asp Pro Tyr Thr Glu Ser Lys Cys Ala
1               5                  10                  15

Thr Cys Cys Gly Gly Arg Gly Lys Cys Val Gly Pro Gln Cys Leu Cys
            20                  25                  30

Asn Arg Ile
        35

<210> SEQ ID NO 26
<211> LENGTH: 36
<212> TYPE: PRT
<213> ORGANISM: Buthus sindicus

<400> SEQUENCE: 26

Cys Gly Pro Cys Phe Thr Lys Asp Pro Glu Thr Glu Lys Lys Cys Ala
```

-continued

```
1               5                   10                  15
Thr Cys Cys Gly Gly Ile Gly Arg Cys Phe Gly Pro Gln Cys Leu Cys
            20                  25                  30

Asn Arg Gly Tyr
            35

<210> SEQ ID NO 27
<211> LENGTH: 35
<212> TYPE: PRT
<213> ORGANISM: Buthus eupeus

<400> SEQUENCE: 27

Met Cys Met Pro Cys Phe Thr Thr Asp His Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
            35

<210> SEQ ID NO 28
<211> LENGTH: 36
<212> TYPE: PRT
<213> ORGANISM: Leiurus quinquestriatus hebraeus

<400> SEQUENCE: 28

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
            35

<210> SEQ ID NO 29
<211> LENGTH: 36
<212> TYPE: PRT
<213> ORGANISM: Leiurus quinquestriatus hebraeus

<400> SEQUENCE: 29

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
            35

<210> SEQ ID NO 30
<211> LENGTH: 35
<212> TYPE: PRT
<213> ORGANISM: Buthus sindicus

<400> SEQUENCE: 30

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
            35

<210> SEQ ID NO 31
<211> LENGTH: 35
<212> TYPE: PRT
```

<213> ORGANISM: Buthus eupeus

<400> SEQUENCE: 31

Met Cys Met Pro Cys Phe Thr Thr Asp Pro Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35

<210> SEQ ID NO 32
<211> LENGTH: 35
<212> TYPE: PRT
<213> ORGANISM: Buthus eupeus

<400> SEQUENCE: 32

Met Cys Met Pro Cys Phe Thr Thr Asp Pro Asn Met Ala Asn Lys Cys
1               5                   10                  15

Arg Asp Cys Cys Gly Gly Gly Lys Lys Cys Phe Gly Pro Gln Cys Leu
            20                  25                  30

Cys Asn Arg
        35

<210> SEQ ID NO 33
<211> LENGTH: 38
<212> TYPE: PRT
<213> ORGANISM: Leiurus quinquestriatus hebraeus

<400> SEQUENCE: 33

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35

<210> SEQ ID NO 34
<211> LENGTH: 36
<212> TYPE: PRT
<213> ORGANISM: Buthus eupeus

<400> SEQUENCE: 34

Met Cys Met Pro Cys Phe Thr Thr Arg Pro Asp Met Ala Gln Gln Cys
1               5                   10                  15

Arg Ala Cys Cys Lys Gly Arg Gly Lys Cys Phe Gly Pro Gln Cys Leu
            20                  25                  30

Cys Gly Tyr Asp
        35

<210> SEQ ID NO 35
<211> LENGTH: 37
<212> TYPE: PRT
<213> ORGANISM: Buthus tamulus

<400> SEQUENCE: 35

Arg Cys Gly Pro Cys Phe Thr Thr Asp Pro Gln Thr Gln Ala Lys Cys
1               5                   10                  15

Ser Glu Cys Cys Gly Arg Lys Gly Gly Val Cys Lys Gly Pro Gln Cys
            20                  25                  30

```
Ile Cys Gly Ile Gln
        35

<210> SEQ ID NO 36
<211> LENGTH: 36
<212> TYPE: PRT
<213> ORGANISM: Buthus eupeus

<400> SEQUENCE: 36

Met Cys Met Pro Cys Phe Thr Thr Asp His Gln Thr Ala Arg Arg Cys
1               5                   10                  15

Arg Asp Cys Cys Gly Gly Arg Gly Arg Lys Cys Phe Gly Gln Cys Leu
            20                  25                  30

Cys Gly Tyr Asp
        35

<210> SEQ ID NO 37
<211> LENGTH: 36
<212> TYPE: PRT
<213> ORGANISM: Mesobuthus tamulus

<400> SEQUENCE: 37

Arg Cys Pro Pro Cys Phe Thr Thr Asn Pro Asn Met Glu Ala Asp Cys
1               5                   10                  15

Arg Lys Cys Cys Gly Gly Arg Gly Tyr Cys Ala Ser Tyr Gln Cys Ile
            20                  25                  30

Cys Pro Gly Gly
        35

<210> SEQ ID NO 38
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: amidated

<400> SEQUENCE: 38

Cys Tyr Gly Pro Gln Cys Leu Cys Asn Arg
1               5                   10

<210> SEQ ID NO 39
<211> LENGTH: 37
<212> TYPE: PRT
<213> ORGANISM: Leiurus quinquestriatus hebraeus

<400> SEQUENCE: 39

Gln Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
        35
```

ABC TRANSPORTER LIGAND GATX1

CROSS-REFERENCE TO RELATED APPLICATION

This application is a filing under 35 U.S.C. §371 of PCT/US2007/069243 filed with the U.S. Receiving Office of the Patent Cooperation Treaty on May 18, 2007, and claims priority to and benefit of U.S. Provisional Application No. 60/801,863 filed on May 19, 2006 by Nael McCarty, Matthew Fuller, and Julia Kubanek, and where permissible is incorporated herein in its entirety.

STATEMENT REGARDING FEDERALLY SPONSORED RESEARCH OR DEVELOPMENT

Aspects of the disclosure were supported in part by Grant No. 7 R01 DK56481-02 award to Nael McCarty by the National Institutes of Health; Grant No. MCB-0224690 awarded to Nael McCarty by the National Science Foundation; and Grant No. MCCART06P0 awarded to Nael McCarty by the Cystic Fibrosis Foundation. Therefore, the US government has certain rights in the claimed subject matter.

FIELD OF THE INVENTION

Aspects of the invention are generally related to ligands for ABC transporters, for example peptide ligands isolated from scorpion venom, pharmaceutical compositions thereof, and methods of use.

BACKGROUND OF THE INVENTION

The ATP-binding cassette (ABC) transporter superfamily contains membrane proteins that translocate a wide variety of substrates across extra- and intracellular membranes, including metabolic products, lipids and sterols, and drugs. Overexpression of certain ABC transporters occurs in cancer cell lines and tumors that are multidrug resistant Genetic variation in. these genes is the cause or contributor to a wide variety of human disorders with Mendelian and complex inheritance including cystic fibrosis, neurological disease, retinal degeneration, cholesterol and bile transport defects, anemia, and drug response phenotypes. Comparison of the human ABC superfamily to that of other sequenced eukaryotes including Drosophila indicated that there is a rapid rate of birth and death of ABC genes and that most members carry out highly specific functions that are not conserved across distantly related phyla.

The ABC transporter family includes cystic fibrosis transmembrane conductance regulator (CFTR). CFTR functions as transporter or channel for chloride ions. Chloride is the predominant physiological anion; therefore, $Cl^-$ channels play critical roles in cell physiology. Plasma membrane $Cl^-$ channels are crucial to the process of secretion in many epithelial tissues such as the kidney, the intestine, and the airway. Plasma membrane $Cl^-$ channels are involved in cell volume regulation in a wide variety of cells. Intracellular $Cl^-$ channels play important roles as anion shunt pathways for endosomal acidification. A $Cl^-$ channel gene is the locus of the primary defect in several human diseases; including Bartter's syndrome, Dent's disease, myotonia, and some forms of epilepsy; $Cl^-$ channel proteins play important roles in a variety of other conditions, including cancer. Despite their central roles in many physiological processes, our understanding of the structures and mechanisms of anion-permeable channels has lagged far behind that of their cation-permeable peers. One clear reason for this discrepancy is a paucity of specific probes that may be useful as tools for studying the permeation pathways and/or gating mechanisms, of $Cl^-$ channels. Indeed, the $Cl^-$ channel blockers available at present work with very low affinity and poor specificity.

Venoms from snakes, scorpions, marine snails, and spiders are rich sources of peptide ligands that have proven to be of great value in the functional exploration of cation channels. Peptide ligands have proven to be among the most potent and selective antagonists available for voltage-gated channels permeable to $K^+$, $Na^+$, and $Ca^{2+}$, and have been very useful tools for detailed structural analysis of these proteins. Pore-blocking toxins provide clues about the arrangement of channel domains, about the interactions between the permeant ions and the pore, and about the proximity and interactions of the gating machinery with the pore. Gating modifiers provide tools to dissect the processes underlying the transitions between gating states. Peptide ligands have high potential as lead compounds for the development of therapeutics targeting pain, diabetes, multiple sclerosis, cardiovascular diseases, and cancer. Because peptide ligands have well-defined structures, constrained by disulfide bridges, they bind with much higher affinity and specificity than other blockers available to date, and report the structures of their targets at molecular detail. Unfortunately, although several potential chloride channel toxins have been identified, peptide inhibitors of chloride channels of an identified molecular target, including CFTR, have not been described.

In 1992, Strichartz and colleagues described the isolation of chlorotoxin (ClTx), a small basic peptide capable of inhibiting low-conductance $Cl^-$ channels from rat colon or brain reconstituted into lipid bilayers. However, neither recombinant ClTx, nor native ClTx isolated from venom, has been shown to block CFTR or any other $Cl^-$ channel of known molecular identity. Native ClTx also had no effect on $Ca^{2+}$-activated $Cl^-$ channels or volume-regulated $Cl^-$ channels, when applied to the bath. Sontheimer and colleagues have shown that ClTx inhibits the migration of glioma cells by inhibition of matrix metalloproteinase-2. A recent study suggests that recombinant ClTx inhibits an endogenous $Ca^{2+}$-activated $Cl^-$ channel in astrocytes, but the molecular identity of this channel is also unknown.

Structure/function studies have led to improved understanding of which parts of the CFTR protein form the permeation pathway, and of the mechanism of binding and hydrolysis of ATP at the NBDs that regulate channel gating. However, little is known about how binding and hydrolysis of ATP controls the conformation of the pore to regulate transitions between open and closed states. The availability of a peptide that interacts with CFTR in a state-dependent manner will allow the application of quantitative approaches previously not accessible for answering these questions.

Therefore, it is an object to provide ABC transporter ligands and methods of their use.

It is another object to provide peptide compositions that interact with CFTR in a state-dependent manner.

It is another object to provide peptide compositions that block or inhibit $Cl^-$ channels.

It is yet another object to provide peptide compositions that block or inhibit $Cl^-$ channels for the manufacture of a medicament.

It is another object to provide pharmaceutical peptide ion channel blockers or inhibitors and methods of use thereof.

It is still another object to provide methods for treating ABC transporter-related disorders with peptide inhibitors of ion channels.

SUMMARY OF THE INVENTION

Compositions and methods of using ABC transporter ligands are provided. In one aspect, the ABC transporter ligand is a scorpion venom peptide having at least 80% sequence identity to CGPCFTTDHQMEQKCAECCG-GIGKCYGPQCLCNR (SEQ ID NO:1) (also referred to as GaTx1). Variants and derivatives of the peptide ligand are also provided. The peptide ligand is believed to have a molecular mass of about 3.7 kDa and interacts with the cystic fibrosis transmembrane conductance regulator. The peptide ligand interacts with cystic fibrosis transmembrane conductance regulator in the interburst state, and reversibly binds to the CFTR when the CFTR is in the closed state. Binding of the peptide to the CFTR locks the chloride channel in the closed state.

In another aspect, the peptide ligand is isolated from *Leiurus quinquestriatus hebraeus* venom.

Another aspect provides a nucleic acid encoding a polypeptide having at least 80% sequence identity to SEQ ID NO:1.

Still another aspect provides a method for reducing ABC transporter activity by contacting the ABC transporter with the disclosed ABC transporter ligands.

Still another aspect provides a method of reducing chloride transport through a chloride channel by contacting the chloride channel with the polypeptide ligand.

Yet another aspect provides a method for treating a disorder or symptom of a disorder related to aberrant chloride channel activity by administering a therapeutically effective amount of the polypeptide ligand. The disorder can be selected from the group consisting of cancer, cystic fibrosis, epilepsy, renal tubular disorders, Bartter's syndrome, Dent's disease, myotonia, osteopetrosis, Angleman or Prader-Willi, upregulation of chloride channels in glioma cells, diarrhea-predominant inflammatory bowel syndrome, autosomal dominant polycystic kidney disease (ADPKD), and secretory diarrhea Another aspect provides an antibody specific for the disclosed peptide ligands.

Figure 1:
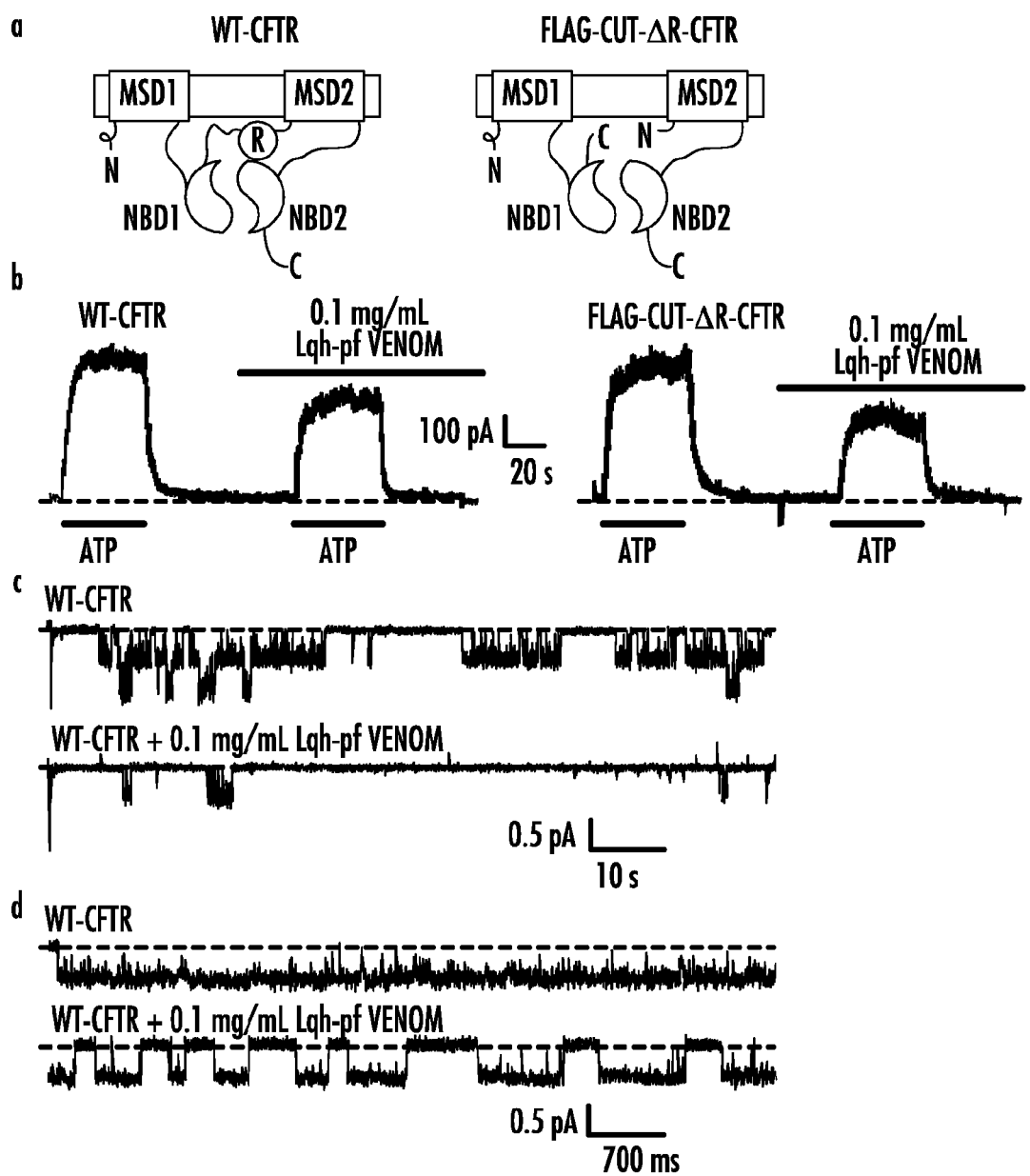
FIG. 1: Scorpion venom inhibits CFTR in a complex manner, (a) Domain architecture of WT-CFTR and Flag-cut-ΔR-CFTR. (b) Representative macropatch traces of WT-CFTR (left) and Flag-cut-ΔR-CFTR (right) in the absence and presence of 0.1 mg/mL equivalent Lqh-pf venom. Venom was applied 30 seconds prior to second exposure to 1 mM MgATP. (c) Representative single channel recording of WT-CFTR with and without 0.1 mg/mL Lqh-pf venom, showing increased interburst closed time. (d) Expanded single channel trace of a WT-CFTR burst in the absence and presence of Lqh-pf venom showing the introduction of venom-induced intraburst closed states.

By "envenomation" is meant when a subject is bitten or stung by a scorpion.

The terms "individual," "host," "subject," and "patient" are used interchangeably herein, and refer to a mammal, including, but not limited to, murines, simians, humans, mammalian farm animals, mammalian sport animals, and mammalian pets.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

"Polypeptide" as used herein refers to an oligopeptide, peptide, modified polypeptide, or protein. Where "polypeptide" is recited-herein to refer to an amino acid sequence of a naturally-occurring protein molecule, "polypeptide" and like terms are not meant to limit the amino acid sequence to the complete, native amino acid sequence associated with the recited protein molecule, but is meant to encompass analogues, degenerate substitutions, etc.

"Polynucleotide" and "nucleic acid" as used interchangeably herein refer to an oligonucleotide, nucleotide, and fragments or portions thereof, as well as to peptide nucleic acids (PNA), fragments, portions or antisense, molecules thereof, and to DNA or RNA of genomic or synthetic origin which can be single- or double-stranded, and represent the sense or antisense strand. Where "polynucleotide" or "nucleic acid" is used to refer to a specific polynucleotide sequence (e.g., encoding a scorpion toxin such as GaTx1), the terms are meant to encompass polynucleotides that encode a polypeptide that is functionally equivalent to the recited polypeptide, e.g., polynucleotides that are degenerate variants, or polynucleotides that encode biologically active variants or fragments of the recited polypeptide.

As used herein, the term "prodrug" refers to an active agent chemically transformed into a per se inactive derivative which, by virtue of chemical or enzymatic attack, is converted to the parent agent within the body before or after reaching the site of action. Prodrugs are frequently (though not necessarily) pharmacologically inactive until converted to the parent drug. A prodrug may be converted into the parent drug by various mechanisms, including enzymatic processes and metabolic hydrolysis. Examples of prodrugs include, but are not limited to, ester and amide prodrugs; polyethylene glycol prodrugs (with and without a linker); N-acyl amine prodrugs, dihydropyridine prodrugs, 2-hydroxybenzamide prodrugs; carbamate prodrugs; peptide prodrugs; Mannich bases, amd Schiff bases.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TAT YGRKKRRQRRR (SEQ. ID NO:3) or RKKRRQRRR (SEQ. ID NO:4); 11 Arginine residues, or positively charged polypeptides or polynucleotides having 8-15 residues, preferably 9-11 residues.

"Subjects" or "patients" as used herein, encompasses any subject or patient amenable to application of the methods of treatment or diagnostic methods. Mammalian subjects and patients, particularly human, subjects or patients, are of particular interest.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

As used herein, the terms "treatment," "treating," and the like, refer to obtaining a desired pharmacologic and/or physiologic effect. The effect may be prophylactic in terms of completely or partially preventing a symptom thereof and/or may be therapeutic in terms of a partial or complete cure for an adverse affect attributable to the condition. "Treatment," as used herein, covers any treatment of an injury in a mammal, particularly in a human, and includes: (a) preventing the injury, arresting any complications, and minimizing its effects; (b) relieving the symptoms; (c) preventing the disease from occurring in a subject which may be predisposed to the disease but has not yet been diagnosed as having it; (d) inhibiting the disease, i.e., arresting its development; and (e) relieving the disease, i.e., causing regression of the disease.

A "substantial portion" of an amino acid or nucleotide sequence refers to an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al, (1993) J. Mol. Biol. 215:403410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification involves amino acid and nucleotide sequences encoding polypeptides that comprise one or more particular scorpion toxin proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

As used herein, "substantially similar" refers to nucleic acid fragments wherein, changes in one or more nucleotide bases results in substitution of one or more amino acids, but do not affect the functional properties of the polypeptide encoded by the polynucleotide sequence. "Substantially similar" also refers to modifications of the nucleic acid fragments of the instant invention such as deletion or insertion of one or more nucleotides that do not substantially affect the functional properties of the resulting protein molecule. It is therefore understood that the invention encompasses more than the specific exemplary sequences.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, UK,). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS, at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95%, 98%, 99% or more identical to the amino acid sequences reported herein.

II. ABC Transporter Ligands

A. Peptide Ligands

One embodiment provides an isolated peptide having at least 80% sequence identity to [1]CGPCFTTDHQMEQK-CAECCGGIGKCYGPQCLCNR[34] (SEQ ID NO:1), a variant, derivative or prodrug thereof. The isolated peptide, also referred to as GaTx1, is isolated from the venom of *Leiurus quinquestriatus hebraeus*, the giant Israeli scorpion. The peptide ligand is believed to have a molecular mass of about 3.7 kDa (FIG. 5a) and binds to ABC transporters, in particular chloride channels. In one embodiment, the ABC transporter is cystic fibrosis transmembrane conductance regulator (CFTR).

The CFTR protein forms a Cl⁻ channel which is activated by protein kinase A (PKA)-mediated phosphorylation plus ATP binding and hydrolysis, and is expressed predominantly in epithelial cells; CFTR is also expressed in ventricular myocytes and multiple regions of the brain. Mutations in CFTR are associated with cystic fibrosis, the most common lethal autosomal recessive disease among Caucasians, affecting >60,000 individuals worldwide. Over-activity of CFTR plays a key role in secretory diarrhea, a worldwide health concern causing thousands of deaths per year, in diarrhea-predominant inflammatory bowel syndrome, and in autosomal dominant polycystic kidney disease (ADPKD), the most common inherited nephropathy and fourth leading cause of end-stage renal disease in the United States. Thus, the disclosed peptide ligands or variants thereof can be used to treat diseases or symptoms related to over-activity of CFTR.

The domain architecture of CFTR (FIG. 1a), with two sets of membrane-spanning domains, two nucleotide-binding domains (NBDs), and a separate regulatory (R) domain, places CFTR in the superfamily of ABC Transporters, although it is the sole member of this family that forms an ion channel. GaTx1 selectively and reversibly inhibits CFTR with higher affinity than other known modulators of this channel by interacting with the protein in the interburst closed state, locking channels closed for minutes at a time. The estimated $K_D$ for GaTx1-mediated inhibition of CFTR is 25 nM in the presence of 0.2 mM ATP.

Another embodiment provides a purified peptide isolated from the venom of *Leiurus quinquestriatus hebraeus* wherein the peptide interacts with CFTR when CFTR is in the interburst closed state. The peptide reversibly interacts or binds with the chloride channel in the closed state and keeps the channel in the closed stated for about 1 second to about 1,2, or 3 minutes.

Another embodiment provides an ABC transporter ligand having an amino acid sequence SEQ ID NO:1, or a biologically active or immunogenic fragment thereof.

Yet another embodiment provides a nucleic acid encoding a polypeptide having at least 0.98% sequence identity to SEQ ID NO:1. The polynucleotide sequence can substituted with the appropriate nucleic acids that encode analogs of the peptide based on codon degeneracy as are known in the art.

Yet another embodiment provides a nucleic acid, having at least 80%, 85%, 90%, 95%, or 99% sequence identity to TGT-GGA-CCT-TGC-TTT-ACA-ACG-GAT-CAT-CAA-ATG-GAA-CAG-AAG-TGT-GCA-GAA-TGT-TGC-GGA-GGC-ATT-GGA-AAA-TGC-TAT-GGT-CGA-CAA-TGT-TTG-TGT-AAT-AGG (SEQ ID NO:2).

B. Variants of ABC Transporter Ligands

1. Conservative Substitutions of Amino Acids

Another embodiment provides nucleic acid molecules that encode a polypeptide having a conservative amino acid change, compared with SEQ ID NO:1. For example, variants can be obtained that contain one or more amino acid substitutions of SEQ ID NO:1, in which an alkyl amino acid is substituted for an alkyl amino acid in a GaTx1 amino acid sequence, an aromatic amino acid is substituted for an aromatic amino acid in a GaTx1 amino acid sequence, a sulfur-containing amino acid is substituted for a sulfur-containing amino acid in a GaTx1 amino acid sequence, a hydroxy-containing amino acid is substituted for a hydroxy-containing amino acid in a GaTx1 amino acid sequence, an acidic amino acid is substituted for an acidic amino acid in a GaTx1 amino acid sequence, a basic amino acid is substituted for a basic amino acid in a GaTx1 amino acid sequence, or a dibasic monocarboxylic amino acid is substituted for a dibasic monocarboxylic amino acid in a GaTx1 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the disclosed peptide ion channel inhibitors. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 of 3).

Particular variants of GaTx1 are characterized by having at least 70%, at least 80%, at least 90%, at least 95% or greater than 95% sequence identity to die corresponding amino acid sequence (e.g., SEQ ID NO:1), wherein the variation in amino acid sequence is due to one or more conservative amino acid substitutions.

Conservative amino acid changes in a GaTx1 gene can be introduced, for example, by substituting nucleotides for the nucleotides recited in SEQ ID NO:2. Such "conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), Directed Mutagenesis: A Practical Approach (IRL Press 1991)). A variant GaTx1 polypeptide can be identified by the ability to specifically bind anti-GaTx1 antibodies.

2. Variants Containing Non-Naturally Occurring Amino Acid Residues

The disclosed peptide antagonists can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., J. Am. Chem. Soc. 113:2722 (1991), Ellman et al., Methods Enzymol. 202:301 (1991), Chung et al. Science 259:806 (1993), and Chung et al., Proc. Nat'l. Acad. Sci, USA 90:10145 (1993).

In a second method, translation is carried out in *Xenopus* oocytes by microinjection of mutated mRNA and chemically aminoacylated suppressor tRNAs (Turcatti et al., J. Biol. Chem. 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395 (1993)).

3. Non-Conservative Amino Acid Substitutions

A limited number of non-conservative amino acids, amino acids that are not encoded by the genetic code, non-naturally occurring amino-acids, and unnatural amino acids may be substituted for GaTx1 amino acid residues.

Essential amino acids in the polypeptides can be identified according to procedures known in the art, such as site-directed mutagenesis or alanine-scanning mutagenesis (Cunningham and Wells, Science 244:1081 (1989), Bass et al., Proc. Nat'l Acad. Sci. USA 88:4498 (1991), Coombs and Corey, "Site-Directed Mutagenesis and Protein Engineering," in Proteins: Analysis and Design, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., J. Biol. Chem. 271:4699 (1996).

Although sequence analysis can be used to further define the GaTx1 anion channel binding region, amino acids that play a role in GaTx1 binding activity (such as binding of GaTx1 to CFTR, or to an anti-GaTx1 antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306 (1992), Smith et al., J. Mol. Biol. 224:899 (1992), and Wlodaver et al., FEBS Lett. 309:59 (1992).

Multiple-amino acid substitutions can be made and tested using known methods of mutagenesis and screening, such as those disclosed by Reidhaar-Olson and Sauer (Science 241:53 (1988)) or Bowie and Sauer (Proc. Nat'l Acad. Sci. USA 86:2152 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832 (1991). Ladner et al., U.S. Pat. No. 5,223,409, Huse, international publication No. WO 92/06204, and region-directed mutagenesis (Derbyshire et al., Gene 46:145 (1986), and Ner et al., DNA 7:127, (1988)). Moreover, GaTx1 labeled with biotin or FITC can be used for expression cloning of GaTx1 ligands.

Variants of the disclosed GaTx1 nucleotide (SEQ ID NO:2) and polypeptide (SEQ ID NO:1) sequences can also be generated through DNA shuffling as disclosed by Stemmer, Nature 370:389 (1994), Stemmer, Proc. Nat'l Acad. Sci. USA 91:10747 (1994), and international publication No. WO 97/20078. Briefly, variant DNA molecules are generated by in vitro homologous recombination by random fragmentation of a parent DNA followed by reassembly using PCR, resulting in randomly introduced, point mutations. This technique can be modified by using a family of parent DNA molecules, such as allelic variants or DNA molecules from different species, to introduce additional variability into the process.

Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-GaTx1 antibodies, can be recovered from the host cells and rapidly sequenced using modern equipment. These methods allow the rapid determination of the importance Of individual amino acid residues in a polypeptide of interest, and can be applied to polypeptides of unknown structure.

4. Fragments of ABC Transporter Ligands

Another embodiment provides "functional fragments" of GaTx1 polypeptides and nucleic acid molecules encoding such functional fragments. Routine deletion analyses of nucleic acid molecules can be performed to obtain functional fragments of a nucleic acid molecule that encodes a GaTx1 polypeptide. As an illustration, DNA molecules having the nucleotide sequence of SEQ ID NO:2 can be digested with Bal31 nuclease to obtain a series of nested deletions. The fragments are then inserted into expression vectors in proper reading frame, and the expressed polypeptides are isolated and tested for the ability to bind anti-GaTx1 antibodies. One alternative to exonuclease digestion is to use-oligonucleotide-directed mutagenesis to introduce deletions or stop codons to specify production of a desired fragment. Alternatively, particular fragments of a GaTx1 gene can be synthesized using the polymerase chain reaction.

This general approach is exemplified by studies on the truncation at either or both termini of interferons have been summarized by Horisberger and Di Marco, Pharmac. Ther. 66:507 (1995). Moreover, standard techniques for functional analysis of proteins are described by, for example, Treuter et al., Molec. Gen. Genet. 240:113 (1993), Content et al., "Expression and preliminary deletion, analysis of the 42 kDa 2-5A synthetase induced by human interferon," in Biological Interferon Systems, Proceedings of ISIR-TNO Meeting on interferon Systems, Cantell (ed.), pages 65-72 (Nijhoff 1987), Herschman, "The EGF Receptor," in Control of Animal Cell Proliferation, Vol. 1, Boynton et al., (eds.) pages 169-199 (Academic Press 1985), Coumailleau et al., J. Biol. Chem. 270:29270 (1995); Fukunaga et. al., J. Biol. Chem. 270:25291 (1995); Yamaguchi et al., Biochem. Pharmacol 50:1295 (1995), and Meisel et al., Plant Molec. Biol. 30:1 (1996).

Another embodiment provides functional fragments of a GaTx1 gene that have amino acid changes, compared with SEQ ID NO:1. A variant GaTx1 gene can be identified, on the basis of structure by determining the level of identity with disclosed nucleotide and amino acid sequences, as discussed above. An alternative approach to identifying a variant gene on the basis of structure is to determine whether a nucleic acid molecule encoding a potential variant GaTx1 gene can hybridize to a nucleic acid molecule comprising a nucleotide sequence, such as SEQ ID NO:2.

One embodiment provides polypeptide fragments or peptides having an epitope-bearing portion of a GaTx1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., Proc. Nat'l Acad. Sci. USA 81:3998; (1983)).

In contrast, polypeptide fragments or peptides may include an "antigenic epitope," which is a region of a protein molecule to which an antibody can specifically bind. Certain epitopes consist of a linear or contiguous stretch of amino acids, and the antigenicity of such .an epitope is not disrupted by denaturing agents. It is known in the art that relatively short synthetic peptides that can mimic epitopes of a protein can be used to stimulate the production of antibodies against the protein (see, for example, Sutcliffe et al., Science 219:660 (1983)). Accordingly, antigenic epitope-bearing peptides and polypeptides of the present invention are useful to raise antibodies that bind with the polypeptides described herein.

Antigenic epitope-hearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a GaTx1 polypeptide, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise ah epitope are described, for example, by Mole, "Epitope Mapping," in Methods in Molecular Biology, Vol. 10, Manson (ed.), pages 105-116 (The Humana Press, Inc. 1992), Price, "Production and Characterization of Synthetic Peptide-Derived Antibodies," in Monoclonal Antibodies: Production, Engineering, and Clinical Application, Ritter and Ladyman (eds.), pages 60-84 (Cambridge University Press 1995), and Coligan et al. (eds.), Current Protocols in Immunology, pages 9.3.1-9.3.5 and pages 9.4.1-9.4.11. (John Wiley & Sons 1997).

For any GaTx1 polypeptide, including variants and fusion proteins, one of ordinary skill in the art can readily generate a fully degenerate polynucleotide sequence encoding that variant. Moreover, those of skill in the art can use standard software to devise GaTx1 variants based upon the nucleotide and amino acid sequences described herein. Accordingly, the present invention includes a computer-readable medium encoded with a data structure that provides at least one of the following sequences: SEQ ID NO:1 and SEQ ID NO:2. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

B. Peptidomimetics

Another embodiment provides peptidomimetics of the ABC transporter ligands, for example SEQ ID NO:1. Peptidomimetics, as used herein, refers to molecules bearing identifiable resemblance to the scorpion venom polypeptide, for example SEQ ID NO:1 that, as a ligand of a chloride channel, can imitate or inhibit the effect of the scorpion venom polypeptide. Exemplary ABC transporter ligand peptidomimetics have increased bioavailability, biostability, bioefficiency, and/or bioselectivity against the biological target of the parent peptide, for example CFTR.

Examples of peptidomimetics have been Isolated as natural products, synthesized as libraries from, novel subunits, and designed on the basis of X-ray crystallographic studies and through an intricate knowledge of the biological mode of action of natural peptides. Examples of such peptidomimetic materials are described in Moore et al., *Chem. Rev.* 101(12), 3893-4012 (2001), Peptidomimetics that structurally and/or functionally resemble a polypeptide embodiment may be made. Several approaches to make peptidomimetics that resemble polypeptides have been described (see, e.g., U.S. Pat. Nos. 5,288,707; 5,552,534; 5,811,515; 5,817,626; 5,817,879; 5,821,231; and 5,874,529).

Peptidomimetic materials of the disclosed ABC transporter ligands can be generated to fall within one of four categories of known peptidomimetics: α-peptides, β-peptides, γ-peptides, and δ-peptides, Copolymers of these peptides can also be used.

Examples of α-peptide peptidomimetics include, but are not limited to, N,N'-linked oligoureas, oligopyrrolinones, oxazolidin-2-ones, azatides and azapeptides.

Examples of β-peptides include, but are not limited to, β-peptide foldamers, α-aminoxy acids, sulfur-containing β-peptide analogues, and hydrazino peptides.

Examples of γ-peptides include, but are not limited to, γ-peptide foldamers, oligoureas, oligocarbamates, and phosphodiesters.

Examples of δ-peptides include, but are not limited to, alkene-based δ-amino acids and carbopeptoids, such as pyranose-based carbopeptoids and furanose-based carbopeptoids.

Other peptidomimetics of the ABC transporter ligands can be oligomers having backbones which can adopt helical or sheet conformations. Example of such compounds include, hut are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo(pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as oligothiophenes with chiral p-phenyloxazoline side chains, and oligo(m-phenylene-ethynylene)s.

Examples of compound containing backbones utilizing hydrogen bonding interactions include, but are not limited to, aromatic amide backbones such as oligo(acylated 2,2',-bipyridine-3,3',-diamine)s and oligo(2,5-bis[2-aminophenyl]pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-phenylene ethynylene)s containing metal-coordinating cyano groups, and hexapyrrins.

C. Vectors and Nucleic Acids Encoding ABC Transporter Ligands

Another embodiment provides nucleic acid compositions that may encode all or a biologically active part of GaTx1, e.g. the nucleic acids may encode all or part of SEQ ID NO:1, and may be synthesized oligonucleotides, mRNA, cDNA, or genomic DNA. These polynucleotides can be used, when in a recombinant expression vector, to produce the encoded GaTx1 or functional fragment thereof. They are also useful as hybridization probes in methods of detecting scorpion venom toxins gene expression, specifically transcription. Accordingly, one embodiment provides recombinant vectors and host cells containing a polynucleotide encoding GaTx1.

Another embodiment provides polynucleotides coding for a scorpion venom toxin polypeptide sequence set forth in SEQ ID NO:1 an identifying sequence thereof. An "identifying sequence" is a contiguous sequence of residues at least about 10 nucleotides (nt) to about 20 nt in length, usually at least about 40 nt to about 55 nt in length, that uniquely identifies the provided sequence. Encompassed in the term "scorpion venom toxin-encoding polynucleotide" are polynucleotides comprising about 10, 20, 25, 50, 72 contiguous nucleotides coding for SEQ ID NO:1, including the entire coding region of SEQ ID NO:2.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., Molecular Cloning: A Laboratory Manual, 2nd Ed. (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., supra, at page 9.50.

Variables to consider when performing, for example, a Southern blot are (1) the complexity of the DMA being blotted and (2) the homology between the target and the sequences being detected. The total amount of the polynucleotides to be studied can vary a magnitude of 10, from 0.1 to 1 μg for a plasmid or phage digest to $10^{-9}$ to $10^{-8}$ μg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 μg of yeast DNA, blotting for two hours, and hybridizing for 4 8 hours with a target polynucleotide radiolabeled with $10^8$ cpm/μg. For a single-copy mammalian gene a conservative approach would start with 10 μg of DNA, blot overnight, and hybridize overnight in the presence of 10% dextran sulfate using a target polynucleotide radiolabeled with greater than $10^8$ cpm/μg, resulting in an exposure time of about 24 hours.

Several factors can affect the melting temperature ($T_m$) of a DNA-DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a. single equation:

$T_m$=81+16.6(log 10Ci)+0.4[% G+C)]−0.6(% formamide)−600/n−1.5(% mismatch), where Ci is the salt concentration (monovalent ions) and n is the length of the hybrid in base pairs (slightly modified from Meinkoth and Wahl, (1984) Anal Biochem. 138:267 284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be, detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of at least about 5×SSC at 65° C., or at least about 4×SSC at 42° C.; see, for example, U.S. Pat. No. 5,707,829, the disclosure of which is herein incorporated by reference.

Generally, hybridization is performed using at least 18 contiguous nucleotides of SEQ ID NO:2. That is, when at least 18 contiguous nucleotides of SEQ ID NO:2 are used as a probe, the probe will preferentially hybridize with a nucleic acid or mRNA comprising the complementary sequence, allowing the identification and retrieval of the nucleic acids of the biological material that uniquely hybridize to the selected probe. Probes of more than 18 nucleotides can be used, e.g. probes of from about 25 nucleotides to about 40 nucleotides, from about 50 nucleotides to about 72 nucleotides, up to the entire coding region can be used, but 18 nucleotides generally represents sufficient sequence for unique identification.

The nucleic acids may also include naturally occurring variants of the nucleotide sequences, e.g. degenerate variants, allelic variants, etc. Variants of the nucleic acids of the invention are identified, by hybridization of putative variants with nucleotide sequences disclosed herein, preferably by hybridization under stringent conditions. For example, by using appropriate wash conditions, variants of the nucleic acids can be identified where the allelic variant exhibits at most about 25-30% base pair mismatches relative to the selected nucleic acid probe. In general, allelic variants contain 15-25% base pair mismatches, and can Contain as few as even 5-15%, or 2-5%, or 1-2% base pair mismatches, as well as a single base-pair mismatch.

Another embodiment provides homologs of GaTx1. Such homologs can be identified by any of a number of methods known to those skilled in. the art. A fragment of the provided nucleic acid may be used as a hybridization probe against a cDNA library front the target organism of interest, where low stringency conditions are used. The probe may be a large fragment, or one or more short degenerate primers.

The homologs corresponding to the nucleic acids encoding SEQ ID NO:1, where, the source of homologous genes can be any related species, within the same genus or group. Within a group, homologs have substantial sequence similarity, e.g. at least 75% sequence identity, usually at least 90%, more usually at least. 95%, preferably 98% or greater between nucleotide sequences. Sequence similarity is calculated based on a reference sequence, which may be a subset of a larger sequence, such as a. conserved motif, coding region, flanking region, etc. A reference sequence will usually be at least about 18 contiguous at long, more usually at least, about 30 nt long, and may extend to the complete sequence that is being compared.

In some embodiments, the polynucleotide includes a nucleotide sequence encoding a polypeptide comprising at least about 5, 10, 15, 20, 25, 50, 75, 100, 125, or 150 of the sequence set forth in SEQ ID NO:1. In other embodiments, the polynucleotide includes a nucleotide sequence encoding the entire polypeptide having the amino acid sequence set forth in any one of SEQ ID NO:1. In still other embodiments, the polynucleotide includes a nucleotide sequence which encodes a polypeptide comprising an amino acid sequence sharing, at least about 60%, preferably at least about 70%, more preferably at least about 80%, even more preferably at least about 87%, 90%, 95%, 98%, or 99% or more amino acid sequence identity with the sequence depicted in SEQ ID NO:1.

As is known to one of skill in the art, using the standard genetic code table, a polynucleotide encoding a subject polypeptide can be designed and using a nucleic acid synthesizer or other means, a polynucleotide encoding a subject polypeptide may be produced.

Various derivatives of an antisense sequence specific for SEQ ID NO:2 may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense polynucleotides, and methods of using such, are described in numerous publications, including, e.g., "Antisense Technology: A Practical Approach" Lichtenstein and Nellen, eds. (1997) IRL Press.

Antisense molecules specific for GaTx1 can be used. to down-regulate expression of sGaTx1 in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by, reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 75, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840 844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in. the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, siRNA, or microRNA etc. may be used to inhibit gene expression. Ribozymes may be synthesized in vitro and administered, or may be encoded on an expression vector, from which the ribozyme is synthesized in targeted cell (for example, see International patent application WO 9523225, and Beigelman et al. (1995) Nucl. Acids Res 23:4434 42). Examples of oligonucleotide with catalytic activity die described in WO 9506764. Conjugates of anti-sense ODN with a metal complex, e.g. terpyridylCu(II), capable of mediating mRNA hydrolysis are described in Bashkin et al. (1995) Appl Biochem Biotechnol 54:43 56.

One embodiment provides an siRNA specific for mRNA encoding GaTx1. Still another embodiment provides a microRNA specific for mRNA encoding GaTx1. Still another embodiment provides a vector encoding a siRNA or microRNA specific for GaTx1 mRNA. Exemplary siRNAs include, but are not limited to those in Table 1 below. One of ordinary skill in the art could readily identify other siRNAs using commercially available software and SEQ ID NO:2.

TABLE 1

Exemplary siRNAs to GaTX1

| GGA-GGC-AUU-GGA-AAA | (SEQ ID NO: 5) |
|---|---|
| U-GGA-CCU-UGC-UUU-A | (SEQ ID NO: 6) |
| GGA-CCU-UGC-UUU-ACA | (SEQ ID NO: 7) |

TABLE 1-continued

Exemplary siRNAs to GaTX1

| ACA-ACG-GAU-CAU-CAA | (SEQ ID NO: 8) |
|---|---|
| -CAG-AAG-UGU-GCA-GA | (SEQ ID NO: 9) |
| -CAA-UGU-UUG-UGU-AA | (SEQ ID NO: 10) |
| CAA-UGU-UUG-UGU-AAU | (SEQ ID NO: 11) |
| -ACA-ACG-GAU-CAU-CA | (SEQ ID NO: 12) |
| GAA-CAG-AAG-UGU-GCA | (SEQ ID NO: 13) |
| G-AAG-UGU-GCA-GAA-U | (SEQ ID NO: 14) |
| -GGA-GGC-AUU-GGA-AA | (SEQ ID NO: 15) |
| UGC-UAU-GGU-CCA-CAA | (SEQ ID NO: 16) |
| A-ACG-GAU-CAU-CAA-A | (SEQ ID NO: 17) |

Another embodiment provides GaTx1 genomic sequences. A genomic sequence of interest includes the nucleic acid present between the initiation codon and the stop codon, including all of the introns that are normally present in a native chromosome. It may further include the 3' and 5' untranslated regions found in the mature in mRNA. It may further include specific transcriptional and translational regulatory sequences, such as promoters, enhancers, etc., including about 1 kb, but possibly more, up to about 6 kb, of flanking genomic DNA at either the 5' or 3' end of the transcribed region. The genomic DNA may be isolated as a fragment of 50 kbp or smaller; and substantially tree of flanking chromosomal sequence. The genomic DNA flanking the coding region, either 3' or 5', or internal regulatory sequences as sometimes found-in introns, contains sequences required for proper tissue and stage specific expression.

The sequence of the 5' flanking region may be utilized for promoter elements, including enhancer binding sites, that provide for regulation in tissues where scorpion toxins polypeptide are expressed. The tissue specific expression is useful for determining the pattern of expression, and for providing promoters that mimic the native pattern of expression. Naturally occurring polymorphisms in the promoter region are useful for determining natural variations in expression.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) Mol. Med, 1:194 205; Mortlock et al. (1996) Genome Res. 6:327 33; and Joulin and Richard-Foy (1995) Eur. J. Biochem, 232:620 626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to one of the subject genes in order to promote expression of wild type or altered scorpion toxin polypeptide, or other proteins of interest in cultured cells.

The nucleic acid compositions may encode all or a part of GaTx1. Double or single stranded fragments of the DNA sequence may be obtained by chemically synthesizing oligonucleotides in accordance with conventional. methods, by restriction enzyme digestion, by PCR amplification, etc For the most part, DNA fragments will be of at least 15 nt, usually at least 25 nt or 35 nt or 45 nt but may he as long as 50 nt 60 nt, 70 nt, 80 nt, and even as long as 90 nt or 100 nt Small DNA fragments are useful as primes for PCR, hybridization screening probes, etc, For use in amplification reactions, such as PCR, a pair of primers will, be used. The exact composition of the primer sequences is not critical to the invention, but for most applications the primers will hybridize to the subject sequence under stringent conditions, as known in the art. It is preferable to choose a pair of primers that will generate an amplification product of at. least about 50 nt, preferably at least about 100 nt. Algorithms for the selection of primer sequences are generally known, and are available in commercial software packages. Amplification primers hybridize to complementary strands of DNA, and will prime towards each other.

The polynucleotides are isolated and obtained in substantial purity, generally as other than an intact chromosome. Usually, the DNA will be obtained substantially free of nucleic acid sequences other than a scorpion venom toxin-encoding polynucleotide, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of scorpion toxin gene expression in the sample.

The sequence of a GaTx1-encoding nucleic acid or gene, including any flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one amino acid, and may differ by at least one or two but not more than about ten amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of clotted genes are known. Examples of protocols for site specific mutagenesis may be found in Gustin et al., Biotechniques 14:22 (1993); Barany, Gene 37:111 23 (1985); Colicelli et al., Mol Gen Genet 199:537 9 (1985); and Prentki et al., Gene 29:303 13 (1984). Methods for site specific mutagenesis can be found in Sambrook et al., Molecular Cloning: A Laboratory Manual, CSH Press 1989, pp. 15.3 15.108; Weiner et al., Gene 126:35 41 (1993); Sayers et al., Biotechniques 13:592 6 (1992); Jones and Winistorfer, Biotechniques 12:528 30 (1992); Barton et al., Nucleic Acids Res 18:7349 55 (1990); Marotti and Tomich, Gene Anal Tech 6:67 70 (1989); and Zhu, Anal Biochem 177:120 4 (1989).

D. GaTx1 Homologs

Homologs and orthologs of scorpion toxin polypeptides, for example GaTx1, are identified by any of a number of methods. A. fragment of scorpion venom toxin polynucleotide or cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C., in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Hybridization methods and conditions are welt known in the art, see, e.g., U.S. Pat. No. 5,707,829. Nucleic acids having a region of substantial identity to a nucleic acid encoding GaTx1, e.g. allelic variants, genetically altered versions of the gene, etc., bind to the GaTx1 sequence under stringent hybridization conditions. By using probes, particularly labeled probes of DNA sequences, one can isolate homologous or related genes. The source of homologous genes can be any species of scorpion or any other organism that produces neurotoxins, e.g., snakes, arachnids, lizards, sea anemones, and the like. Between scorpion species, homologs have substantial sequence similarity, i.e. at least 75% sequence identity between nucleotide sequences, in some cases 80 or 90% sequence identity, and may be as high as 95%, 98%, or 99% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at. least about 30 nt long, and may extend to the complete sequence that is being compared. Algorithms for sequence analysis are known in the art, such as BLAST, described in Altschul et. al. (1990) J. Mol. Biol. 215:403 10.

E. Pharmaceutical Compositions

Pharmaceutical compositions including an ABC transporter ligand such as GaTx1 peptide are provided. Conditions alleviated or modulated by the administration of such compositions include those indicated below. Such pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, pharmaceutical compositions are provided including effective amounts, of a GaTx1 peptide, or derivative products, and pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., TWEEN 20, TWEEN 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, e.g. Remington's Pharmaceutical Sciences, 18th Ed. (1990, Mack publishing Co., Eastern. Pa, 18042) pages 1435-1712 which are herein incorporated by reference. The compositions may be prepared in liquid form, or may be in dried powder (e.g., lyophilized) form.

1. Oral Delivery

GaTx1 peptide can be formulated for oral delivery. Oral solid dosage forms are described generally in Remington's. Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the ABC transporter ligands (or chemically modified forms thereof) and inert ingredients which allow for protection against the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. As discussed above, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidine, polyproline, poly-1,3-dioxolane and poly-1,3,6-tioxocane [see, e.g., Abuchowski and Davis (1981) "Soluble Polymer-Enzyme Adducts," in Enzymes as Drugs. Hoeenberg and Roberts, eds. (Wiley-Interscience; New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as an the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, .alpha.-lactose, anhydrous lactose, cellulose, sucrose, modified dextrans and starch. Certain inorganic salts may be also be used, as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered, gums may be used as disintegrants and as binders and can include powdered gums such as agar, Karaya or tragacanth. Alginic acid and its sodium salt are also useful as disintegrants.

Binders may be used to hold die peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidine (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogoi 400, polyoxyl 40 stearate, polyoxyethylene hydrogenated castor oil 10, 50 and 60, glycerol monostearate, polysorbate 20, 40, 60, 65 and 80. sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

2. Parenteral Delivery

Preparations according to this invention for parenteral administration include sterile aqueous of non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by beating the compositions. They can also be manufactured using sterile water, or some other sterile injectable medium, immediately before use.

3. Rectal or Vaginal Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

4. Pulmonary Delivery

Also contemplated herein is pulmonary delivery of the GaTx1 peptides for derivatives thereof). The peptide (or derivative) is delivered to the kings of a mammal while inhaling and traverses across the lung epithelial lining to the blood, stream [see, e.g., Adjei, et al. (1990) Pharmaceutical Research 7:565-569; Adjei, et al. (1990) Int. J, Pharmaceutics 63; 135-144 (leuproiide acetate); Braquet, et al. (1989) J. Cardiovascular Pharmacology 13(sup5):143-146 (endothelin-1); Hubbard, et al. (1989) Annals of Internal Medicine, Vol. III, pp. 206-212 ($\alpha$1-antitrypsin); Smith, et al. (1989) J. Clin. Invest. 84:1145-1146 (.alpha.-1-proteinase); Oswein, et al. (1990) "Aerosolization of Proteins", Proceedings of Symposium on Respiratory Drug Delivery II Keystone, Colo. (recombinant human growth hormone); Debs, et al, (1988) J. Immunol. 140:3482-3488 (interferon-.gamma. and tumor necrosis factor .alpha.); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices suitable for the practice of this invention are the Ultravent nebulizer (Mailinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.).

All such devices require the use of formulations suitable for the dispensing of peptide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally include a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetratfluoroethane, or combinations thereof. Suitable surfactants include sorbitan trioleate and soya lecithin. Oleic acid may also be useful as a surfactant.

Formulations for dispensing from a powder inhaler device will include a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The peptide (or derivative) should most advantageously be prepared in particulate form with an average particle size of less than 10 mm (or microns), most preferably 0.5 to 5 mm, for most effective delivery to the distal lung.

5. Nasal Delivery

Nasal of the ABC transporter ligand (or derivatives) is also contemplated. Nasal delivery allows the passage of the peptide to the blood stream directly after administering the therapeutic product to the nose, without the necessity for deposition of the product in the lung. Formulations for nasal delivery include those with dextran or cyclodextran.

Other penetration-enhancers used to facilitate nasal delivery are also contemplated for use with the peptides of the present invention (such as described in International Patent Publication No. WO 2004056314, filed Dec. 17, 2003, incorporated herein by reference in its entirety).

6. Dosages

For all of the peptide compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

7. Polymeric Matrices

Both non-biodegradable and biodegradable matrices can be used for delivery of ABC transporter ligands such as GaTx1 peptides, although biodegradable matrices are preferred. These may be natural or synthetic polymers, although synthetic polymers are preferred due to the better characterization of degradation and release profiles. The polymer is selected based on the period over which release is desired. In some cases linear release, may be most useful, although in others a pulse release or “bulk release” may provided more effective results. The polymer may be in the form of a hydrogel (typically in absorbing up to about 90% by weight of water), and can optionally be crosslinked with multivalent ions or polymers.

Representative synthetic polymers that can be used for delivery include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone., polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxy propyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene add polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho) esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

The matrices can be formed by solvent evaporation, spray drying, solvent extraction and other methods known to those skilled in the art.

Bioerodible microspheres can be prepared using any of the methods developed for making microspheres for drug delivery, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci, 35, 755-774 (1988). The selection of the method depends on the polymer selection, the size, external morphology, and crystallinity that is desired, as described, for example, by Mathiowitz, et al. Scanning Microscopy 4, 329-340 (1990); Mathiowitz, et al., J. Appl. Polymer Sci. 45, 125-134 (1992); and Benita, et al., J. Pharm. Sci, 73, 1721-1724 (1984). In solvent evaporation, described for example, in Mathiowitz, et al., (1990), Benita, and U.S. Pat. No. 4,272,398 to Jaffe, the polymer is dissolved in a volatile organic solvent. The peptide either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. In general, the polymer can be dissolved in methylene chloride. Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of peptides. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000. Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to malic microspheres from polymers with high melting points and a wide range of molecular weights. Microspheres having a diameter between one and 300 microns can be obtained with this procedure. The external morphology of the spheres is highly dependent on the type of polymer used. In spray drying, the polymer is dissolved in methylene chloride (0.04 g/ml), A known amount of active drug is suspended (if insoluble) or co-dissolved (if soluble) in the polymer solution. The solution or the dispersion is then spray-dried. Double walled microspheres can be prepared according to U.S. Pat. No. 4,861,627 to Mathiowitz.

Hydrogel microspheres made of gel-type polymers such as alginate or polyphosphates or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., Pharmazeutische Industrie 40-11A, 1230 (1978). Chitosan microspheres can be prepared by dissolving the polymer in acidic solution and crosslinking with tripolyphosphate. For example, carboxymethylcellulose (CMC) microsphere are. prepared by dissolving the polymer in an acid solution and precipitating the microspheres with lead ions. Alginate/polyethylene imide (PEI) can be prepared to reduce the amount of carboxyl groups on the alginate microcapsules.

Other delivery systems including films, coatings, pellets, slabs, and devices can be fabricated using solvent or melt casting, and extrusion, as well as standard methods for making composites. The polymer can be produced by first mixing monomers and peptides as described by Sawhney, et al., and polymerizing the monomers with UV light. The polymerization can be carried out in vitro as well as in vivo.

F. Fusion Proteins

Another embodiment provides a fusion protein including GaTX1 or a biologically active fragment thereof is fused to a heterologous peptide or protein. A fusion protein is a protein created through genetic engineering from two or more proteins/peptides. This is achieved by creating a fusion gene: removing the stop codon from the DNA sequence of the first protein, then appending the DNA sequence of the second protein in frame. That DNA sequence will then be expressed by a cell as a single protein.

In one embodiment a linker (or "spacer") peptides are also added which make it more likely that the proteins fold independently and behave as expected. Especially in the case where the linkers enable protein purification, linkers in protein or peptide fusions can be engineered with cleavage sites for proteases or chemical agents which enable the liberation of the two separate proteins.

The disclosed fusion proteins are useful for identification and purification of GaTx1, by fusing a GST protein, FLAG peptide, or a hexa-his peptide (a 6xhis-tag) which can be isolated using nickel or cobalt resins (affinity chromatography).

in one embodiment GaTx1 or derivative thereof can be fused to a cytotoxic moiety such as ricin, saporin, or *pseudonomas* exotoxin. Such fusion proteins can be useful for delivering cytotoxic materials to cells with chloride channels.

In another embodiment GaTx1 peptide can be labeled with a radioisotope. For example $I^{125}$, fluorophore, or other detectable agent. Labeled GaTx1 can be useful for detecting chloride channels in a biological sample, in particular for detecting CFTR, or for the selective ablation of cells overproducing CFTR.

Still another embodiment provides an ABC transporter ligand fused to protein transduction domain, localization signal or both. Protein transduction domains include but are not limited to HIV TAT YGRKKRRQRRR (SEQ. ID NO. 3) or RKKRRQRRR (SEQ. ID NO. 4); 11 Arginine residues, or positively charged polypeptides or polynucleotides having 8-15. residues, preferably 9-11 residues, Antp SGRQIKIW-FQN-RRMKWKKC (SEQ ID NO:18), and HIV Tat SGYGRKKRRQRRRC (SEQ ID NO:19).

The ABC transporter ligand can be operably linked to an antibody or antigen-binding fragment of the antibody so that the ABC transporter ligand can be selectively delivered to a target expressing an epitope recognized by the antibody. The antibody can be a single chain antibody, monoclonal antibody, polyclonal antibody, humanized antibody, or chimeric antibody.

III. Methods of Manufacture

A. Purification

A bioassay-guided fractionation of Lqh venom may be used to isolate a peptide ligand that interacts with ABC transporters, for example CFTR ion channels. The fractionation approach may include, for example, the following steps: homogenization to disrupt mucus contained in the venom, recovery of components below 10 kDa molecular weight by separation through a centrifuge filter resulting in "Lqh-pf venom", testing for activity against the ion channel expressed in *Xenopus* oocytes, using recordings from inside-out single-channel patches or macropatches, initial fractionation according to hydrophobicity by reversed-phase HPLC(RP-HPLC) in a gradient of acetonitrile in water, testing fractions for activity against CFTR expressed in *Xenopus* oocytes, using recordings from inside-out single-channel patches or macropatches, secondary fractionation according to molecular weight by size-exclusion using gel filtration chromatography, desalting of fractions using RP-HPLC, with collection of individual chromatographic peaks, testing for activity against the ion channel expressed in *Xenopus* oocytes, using recordings from inside-out single-channel patches and/or macropatches, characterization of material represented in individual chromatographic peak using MALDI-TOF, and breaking of the disulfide bridges in the isolated toxin by reduction and subsequent carboxymethylation of free cysteines. The primary sequence may be determined using Edman degradation, but any known method of amino acid sequences may be used.

B. Synthesis of ABC Transport Ligands

Certain embodiments provide peptides that selectively bind to ABC transporters including anion channels and inhibit the transport anions through the channel. These peptide ligands of anion channels can be synthesized using general methods, for peptide synthesis and purification, and disulfide bond formation, known in the art. As described in the Examples, linear peptides, were produced by solid phase synthesis using 9-fluorenylmethoxycarbonyl (Fmoc) chemistry. Coupling of Fmoc amino acids was performed using the HBTU/HOBT/DIPEA method on an Applied Biosystems 431A synthesizer. The purified linear peptide was subjected to oxidative cyclization under equilibrating conditions in order to promote formation of the most stable disulfide bridges, with the reaction being monitored by analytical HPLC. Cyclized peptide was isolated from the acidified reaction mixture by reversed phase extraction, was purified by HPLC, and was characterized by MALDI-MS for molecular weight determination (FIG. 8) and by analytical HPLC (FIG. 9) for comparison with the native toxin.

Another embodiment provides polypeptides having 80%, 85%, 90%, 95%. or 98% sequence identity or greater to SEQ ID NO:1, preferably having 99% sequence identity or greater to SEQ ID NO:1 optionally where one or more amino acids are modified, such as by incorporation of biotin, or are substituted by non-natural amino acids.

Synthetic peptides representing portions of the instant amino acid sequences may be synthesized by solid-phase chemistry. Alternatively, toxin peptides may be produced by recombinant methods upon expression in prokaryotic or eukaryotic cells. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1-34; Maniatis).

IV. Methods of Using ABC Transporter Ligands

A. Methods of Treatment

Diseases, disorders, or symptoms of disease or disorders related to aberrant ABC transporter activity can be treated using the disclosed ABC transporter ligands. For example, diseases associated with defective or overactive ion channels, in particular chloride channels can be treated using the disclosed peptides and peptide compositions. One embodiment provides a method of treating a subject by administering to the subject an effective amount of the pharmaceutical composition including a therapeutically effective amount of a ABC transporter ligand, for example GaTx1, a variant or a pharmaceutically acceptable salt or solvate thereof. By "pharmaceutically acceptable salts" is meant any salts that are known or later discovered to be pharmaceutically acceptable. Some examples are: acetate; trifluoroacetate; hydrohalides, such as hydrochloride and hydrobromide; sulfate; citrate; maleate; tartrate; glycolate; gluconate; succinate; mesylate; besylate; and oxalate salts. Some diseases attributed to defective, aberrant or overactive ion channels, in particular overactive chloride ion channels includes cancer, cystic fibrosis, epilepsy, renal tubular disorders. Bartter's syndrome, Dent's disease, myotonia, osteopetrosis, Angleman or Prader-Willi, upregulation of chloride channels k glioma cells, diarrhea-predominant inflammatory bowel syndrome, secretory diarrhea, and in autosomal dominant polycystic kidney disease (ADPKD).

Another embodiment provides a method of treating a disorder or a symptom of disorder selected from the group consisting of cancer, cystic fibrosis, epilepsy, renal tubular disorders, Barrier's syndrome, Dent's disease, myotonia, steopetrosis, Angleman or Prader-Willi, upregulation of chloride channels in glioma cells, diarrhea-predominant inflammatory bowel syndrome, autosomal dominant polycystic kidney disease (ADPKD), secretory diarrhea by administering to a host in need thereof an effective amount of GaTx1, a variant, derivative, or a prodrug thereof.

The roost common genotype among cystic fibrosis (CF) patients in this country, by far, is the ΔF508 mutation, which leads to the deletion (Δ) of the phenylalanine at position 508. This single genotype (one of >1500 mutations known in the CFTR gene) is found on at least one chromosome in some 67% of CF patients in this country. CFTR proteins bearing the ΔF508 mutation are recognized as misfolded during the protein processing pathway that every newly-made protein follows. Chaperone proteins interact with this part of the CFTR protein (and others), and sense that it is misshaped in the ΔF508-CFTR. When this happens, processing along the productive pathway stops, and the new protein is degraded. Because the affinity of GaTx1 for CFTR is higher than the affinity of the chaperone proteins for CFTR, GaTx1 can compete with chaperone proteins for binding sites on CFTR and thereby prevent or reduce the binding of chaperone proteins to CFTR allowing the protein to continue through the processing pathway. Hence, GaTx1 may overcome the trafficking defect associated with ΔF508-CFTR.

Thus, another embodiment provides a method of reducing chaperone protein interaction with CFTR by contacting the CFTR with an ABC transporter ligand such as GaTx1.

Yet another embodiment provides a method for reducing ABC transporter activity by contacting die ABC transporter with a ligand having at least 80% sequence identity to SEQ ID NO:1.

Another embodiment provides a method for reducing chloride channel function by contacting the chloride channel with a GaTx1 peptide, variant, derivative or prodrug thereof.

Still another embodiment provides a method for treating a disorder or symptom of a disorder related to an overactive chloride channel including administering a pharmaceutical composition including an effective amount of GaTx1, a derivative, variant or prodrug thereof. The administration of a peptide ligand obtained from scorpion venom is believed to act to lock closed chloride channels, for example CFTR, and thereby reduce chloride ion transport through chloride channels.

Another embodiment provides a method for reducing chloride ion transport through CFTR by contacting CFTR with a peptide ligand or biologically active fragment thereof isolated from scorpion venom. The scorpion venom peptide ligand can be GaTx1 or a biologically active fragment thereof.

Another embodiment provides a method of inhibiting an ABC transporter or a domain thereof CFTR by contacting the ABC transporter with GaTx1, a variant thereof a derivative thereof, or a biologically active fragment thereof.

ABC transporters include polypeptides encoded by the following genes; ABCA1, ABCA2, ABCA3, ABCA4, AABCA5, ABCA6, ABCA7, ABCA8, ABCA9, ABCA10, ABCA12, ABCA13, ABCB1, ABCB2, ABCB3, ABCB4, ABCB5, ABCB6, ABCB7, ABCB8, ABCB9, ABCB10, ABCB11, ABCC1, ABCC2, ABCC3, ABCC4, ABCC5, ABCC6, CFTR, ABCC8, ABCC9, ABCC10, ABCC11, ABCC12, ABCD1, ABCD2, ABCD4, ABCE1, ABCF1, ABCF2, ABCF3, ABCG1, ABCG2, ABCG4, and ABCG5. In one embodiment the GaTx1 is ligand for one or more ABC transporters.

B. Detection Methods

Various embodiments provide a variety of detection methods, which methods are useful in diagnostic assays. Also provided are a variety of screening assays, which assays are useful for identifying agents which affect ABC transporter ligand activity (e.g., ion channel binding) and/or ABC transporter ligand mRNA and/or polypeptide levels.

Detection methods include methods for detecting ABC transporter ligands in a biological sample, methods for detecting ABC transporter ligand mRNA in a biological sample, and methods for detecting ABC transporter ligand-ion channel binding in a biological sample.

1. Methods of Detecting GaTx1 in a Biological Sample

Other embodiments provide methods for detecting the presence and/or measuring a level of an ABC transporter ligand, for example GaTx1, in a biological sample, using a ABC transporter ligand-specific antibody. The methods generally include:

a) contacting the sample with an antibody specific for GaTx1; and b) detecting binding between the antibody and molecules of the sample.

Detection of specific binding of the GaTx1-specific antibody, when compared to a suitable control, is an indication that ABC transporter ligands are present in the sample. Suitable controls include a sample known not to contain a ABC transporter ligand (GaTx1); and a sample contacted with an antibody not specific for a s ABC transporter ligand, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the scorpion venom toxin polypeptide-specific antibody will be detectably labeled, either directly or indirectly. Direct labels include radioisotopes; enzymes whose products are delectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for scorpion venom toxin polypeptide-specific antibodies, wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled scorpion venom toxin polypeptide-specific antibody. Detection methods are known in the art and will be chosen as appropriate to the signal emitted by the detectable label. Detection is generally accomplished in comparison to suitable controls, and to appropriate standards.

Still other embodiments provide methods for detecting the presence and/or measuring a level of GaTx1 in a biological sample. The methods generally comprise:

a) contacting the sample with an ABC transporter, for example CFTR protein or fragment thereof; and b) detecting binding between the ABC transporter and molecules of the sample.

Detection of specific binding of the ABC transporter is an indication that GaTx1 polypeptides are present in the sample.

Methods for detecting binding between a ABC transporter ligand and an ABC transporter are known in the art and include immunoprecipitation of ABC transporter-ligand complexes using an antibody specific to the ABC transporter ligand or ABC transporter, as long as the antibody does not disrupt s ABC transporter ligand -ABC transporter binding. Alternatively, the ion channel polypeptide used may be a fusion protein which provides for specific immunoprecipitation of the fusion partner, an enzymatic detection, a fluorescent signal (e.g., a green fluorescent protein). The ion channel, polypeptide can be labeled with any detectable label, as described below. The ion channel polypeptide can be attached, directly or through a linker, to an insoluble support (e.g., polystyrene beads, magnetic beads, and the like), thereby providing a means for separating scorpion toxin family polypeptide-ion channel/receptor complexes from the biological sample, and subsequently detecting the presence of and/or measuring the amount (level) of scorpion venom toxin polypeptide.

Binding of ABC transporter ligand to the ion channel may also be detected by monitoring ion channel activity, using methods such as electrophysiology (two electrode voltage clamp or single electrode patch clamp), guanidinium ion flux assays, toxin-binding assays, and Fluorometric Imaging Plate Reader (FLIPR) assays. (See, e.g., Sullivan, et al. (1999) Methods Mol. Biol. 114:125 133; Siegel and Isacoff (1997) Neuron 19:1 20; and Lopatin, et al. (1998) Trends Pharmacol. Sci. 19:395 398.)

2. Methods of Detecting GaTx1 mRNA in a Biological Sample

One embodiment provides methods for detecting the presence of ABC transporter ligand mRNA in a biological sample. The methods can be used, for example, to assess whether a test compound affects ABC transporter ligand gene expression, directly or indirectly.

An exemplary method generally includes:

a) contacting the sample with a ABC transporter ligand-encoding polynucleotide under conditions which allow hybridization; and b) detecting hybridization, if any.

Detection of hybridization, when compared to a suitable control, is an indication of the presence in the sample of a ABC transporter ligand-encoding polynucleotide, for example a GaTx1-encoding polynucleotide. Appropriate controls include, for example, a sample which is known not to contain s ABC transporter ligand -encoding polypeptide mRNA, and use of a labeled polynucleotide of the same "sense" as a ABC transporter ligand mRNA. Conditions which allow hybridization are known in the art, arid have been described in more detail above. Detection can be accomplished by any known method, including, but not limited to in situ hybridization, PCR, RT-PCR, and "Northern" or RNA blotting, or combinations of such techniques, using a suitably labeled ABC transporter ligand polynucleotide, A variety of labels and labeling methods for polynucleotides are known in the art and can be used in the assay methods of the invention. Specific hybridization can be determined by comparison to appropriate controls.

Methods using PCR amplification can be performed on die DNA from a single cell, although it is convenient to use at least about 105 cells. The use of the polymerase chain reaction is described in Saiki et al. (1985) Science 239:487, and a review of current techniques may be found in Sambrook, et al. Molecular Cloning: A Laboratory Manual, CSH Press 1989, pp. 14.2B14.33. A detectable label may he included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4=,5=-dichloro-6-carboxyfluorescein (JOE), 6-carboxy-X-rhodamine (ROX), -6-carboxy-2',4',7',4,7-hexachlorofluorescein (HEX), 5-carboxyfluorescein (5-FAM) or N,N,N=,N=tetramethyl-6-carboxyrhodamine (TAMRA). radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

C. Research Tools

The disclosed peptide ABC transporter ligands can be used to investigate ABC transporter structure and function. For example, GaTx1 can be used as a structural probe of the CFTR protein or its domains, or any other member of the ABC transporter superfamily, or their domains. For example, GaTx1, or a derivative of GaTx1, can be used to stabilize the conformation of CFTR protein, or its domains, or any other member of the ABC transporter superfamily, or their domains, in crystallization experiments.

Additionally, GaTx1, or a derivative of GaTx1, can be used to isolate CFTR, or its domains, or any other member of the ABC transporter superfamily, or their domains, by way of affinity chromatography wherein GaTx1, or a derivative of GaTx1, is coupled to a solid support.

V. Screening Assays

Another embodiment provides screening methods for identifying agents which modulate s ABC transporter ligand-ABC transporter binding activity such as GaTx1-ABC transporter binding activity, methods for identifying agents which GaTx1-ABC transporter interaction, methods for identifying agents which modulate a level of GaTx1 in a cell, and methods for identifying agents which -modulate a level of GaTx1 mRNA in a cell.

As used herein, the terra "modulate" encompasses "increase" and "decrease". Of particular interest are agents which modulate GaTx1-ABC transporter binding activity, and/or which modulate GaTx1-ion channel interaction, and/or which modulate a level of ABC transporter ligand in a cell, and/or which modulate a level of GaTx1 mRNA in a cell. Such agents are of interest as candidates for treating diseases or disorders associated with ion channels, including, but not limited to diose associated with chloride channels (e.g., epilepsy, renal tubular disorders, Bartter's syndrome, cystic fibrosis, osteopetrosis, Angleman or Prader-Willi, upregulation of chloride channels in glioma cells, etc.), sodium channels (e.g., Hyperkalemic periodic paralysis, hypokalemic periodic paralysis, congenital Paramyotonia, Myotonia Fluctuant, Myotonia Permanens, Acetazolamide-responsive myotonia, malignant hyperthermia, nerve injury, epilepsy, various heart diseases, thyroid, endocrine, etc.).

The terms "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted, with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Furthermore, pharmacophores may be designed based on the structural aspects of the ion channel/receptor binding interfaces of scorpion venom toxin polypeptides.

Where the screening assay is a binding assay, one or more of the molecules may be joined to a label where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding, and/or reduce non-specific or background interactions. Reagents that improve the efficiency of the assay, such as protease inhibitors, nuclease inhibitors, anti-microbial agents, etc, may be used. The components can be added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

1. Methods for Identifying Agents that Modulate Scorpion Venom Polypeptide-Ion Channel Binding Activity One embodiment provides methods of identifying agents which modulate ABC transporter binding activity of ABC transporter ligands. The term "modulate" encompasses an increase or a decrease In the measured ABC transporter ligand-ABC transporter binding activity when compared to a suitable control.

The method generally comprises:

a) contacting a substance to be tested, with a sample containing a ABC transporter ligand such as GaTx1 and an ABC transporter such as a chloride ion channel; and b) measuring ABC transporter binding activity of the ABC transporter ligand in the presence of the substance.

An increase or a decrease in ABC transporter binding activity in comparison to ABC transporter binding activity in a suitable control (e.g., a sample including ABC transporter ligand and an ABC transporter in the absence of the substance being tested) is an indication that the substance modulates a ABC transporter binding activity of the ABC transporter ligand.

Methods for practicing such assays are known to those of skill in the art. (See, e.g., Mishina et al. (1985) Nature 313: 364 369; and Noda, et al. Nature 322:836 828.) For example, ion channel activity may be measured by methods such as electrophysiology (two electrode voltage clamp or single electrode patch clamp), guanidinium ion flux assays, toxin-binding assays, and Fluorometric Imaging Plats Reader (FLIPR) assays. (See, e.g., Sullivan, et al. (1999) Methods Mol. Biol. 114:125 133: Siegel and Isacoff (1997) Neuron 19:1 20; and Lopatin, et al. (1998) Trends Pharmacol. Sci. 19:395 398.)

An "agent which modulates ABC transporter-ABC transporter ligand binding activity", as used herein, describes any molecule, e.g. synthetic or natural organic or inorganic compound, protein or pharmaceutical, with the capability of altering ABC transporter binding activity of a ABC transporter ligand, as described herein. Generally a plurality of assay mixtures are run in parallel with different agent concentrations to obtain a differential response to the various concentrations. Typically, one of these concentrations serves as a negative control, i.e. at zero concentration or below the level of detection. Ion channel binding can be measured as described hereinabove.

An agent which modulates ABC transporter binding activity of a ABC transporter ligand increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

2. Methods of Detecting Agents which Modulate a Level of Scorpion Venom Toxin Polypeptide mRNA and/or Polypeptide A wide variety of cell-based assays may be used for identifying agents which modulate levels of ABC transporter ligand polypeptide mRNA, using, for example, a mammalian cell transformed with a construct including a ABC transporter-encoding cDNA such that the cDNA is overexpressed, or, alternatively, a construct including a ABC transporter gene promoter operably linked to a reporter gene.

Accordingly, one embodiment provides a method for identifying an agent, particularly a biologically active agent, that modulates a level of ABC transporter ligand expression in a cell, the method including: combining a candidate agent to be tested with a cell comprising a nucleic acid which encodes a ABC transporter ligand; and determining the effect of said agent on ABC transporter ligand expression. A modulation, of ABC transporter ligand expression, levels includes increasing the level and decreasing the level of ABC transporter ligand mRNA and/or scorpion venom toxin encoded by the scorpion venom toxin polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of ABC transporter ligand mRNA and/or polypeptide following contacting the cell with a candidate agent being tested, compared to a control to which no agent is added, is an indication that the agent modulates ABC transporter ligand expression.

An agent being tested for its effect on ABC transporter ligand expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetraxolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures.

Scorpion venom toxin family polypeptide mRNA and/or polypeptide whose levels are being measured can be encoded by an endogenous scorpion venom toxin polynucleotide, or the scorpion venom toxin polynucleotide can be one that is comprised within a recombinant vector and introduced into the cell, i.e., the ABC transporter ligand mRNA and/or polypeptide can be encoded by an exogenous scorpion venom toxin polynucleotide. For example, a recombinant vector may comprise an isolated ABC transporter ligand transcriptional regulatory sequence, such as a promoter sequence, operably linked to a reporter gene (e.g., β-galactosidase, CAT, luciferase, or other gene that can be easily assayed for expression). In these embodiments, the method for identifying an agent that modulates a. level of ABC transporter ligand expression in a cell, comprises: combining a candidate agent to be tested with a cell comprising a nucleic acid which comprises a scorpion venom toxin gene transcriptional regulatory element operably linked to a reporter gene; and determining the effect of said agent on reporter gene expression. A recombinant vector may comprise an isolated ABC transporter ligand transcriptional regulatory sequence, such as a promoter sequence, operably linked to sequences coding for a ABC transporter ligand; or the transcriptional control sequences can be operably linked to coding sequences for a scorpion venom toxin fusion protein comprising ABC transporter ligand fused to a polypeptide which facilitates detection. In these embodiments, the method comprises combining a candidate agent to be tested with a cell comprising a nucleic acid which comprises a scorpion venom toxin gene transcriptional regulatory element operably linked to a ABC transporter ligand-coding sequence; and determining the effect of said agent on ABC transporter ligand expression, which determination can be carried out by measuring an amount of ABC transporter ligand mRNA, ABC transporter ligand, or scorpion venom toxin fusion polypeptide produced by the cell.

Cell-based assays generally comprise the steps of contacting the cell with an agent to be tested, farming a test sample, and, after a suitable time, assessing the effect of the agent on ABC transporter ligand expression. A control sample comprises the same cell without the candidate agent added. ABC transporter ligand expression levels are measured in both die test sample and the control sample. A comparison is made between ABC transporter ligand expression level in the test sample and the control sample. ABC transporter ligand expression can be assessed using conventional assays. For example, when a mammalian cell line is transformed with a construct that results in expression of ABC transporter ligand, ABC transporter ligand mRNA levels can be detected and measured, as described above, or ABC transporter ligand levels can he detected and measured, as described above. A suitable period of time for contacting the agent with the cell can be determined empirically, and is generally a time sufficient to allow entry of the agent into the cell and to allow the agent to have a measurable effect on ABC transporter ligand mRNA and/or polypeptide levels. Generally, a suitable time is between 10 minutes and 24 hours, more typically about 18 hours. Methods of measuring ABC transporter ligand mRNA levels are known in the art, several of which have been described above, and any of these methods can be used in the methods of the present invention to identify an agent which modulates ABC transporter ligand mRNA level in a cell, including, but not limited to, a PCR, such as a PCR employing detectably labeled oligonucleotide primers, and any of a variety of hybridization assays. Similarly, ABC transporter ligand levels can be measured using any standard method, several of which have been described herein, including, but not limited to, an immunoassay such as ELISA, for example an ELISA employing a detectably labeled antibody specific for a ABC transporter ligand.

VI. Preparation of Antivenom and Antibodies

Identification of potent components is an important first step in designing and obtaining effective antivenom. Antibodies raised against the critical toxic components have the potential to block the toxic effects and reduce the pain associated with the scorpion envenomation. Antibodies that specifically bind to scorpion venom toxin polypeptides, in particular to GaTx1 are produced by; 1) immunization of non-human animals with the isolated cells and production of hybridomas; and 2) identification of antibodies that specifically bind scorpion venom toxin polypeptides (e.g., by screening hybridoma supernatants with scorpion venom toxin). Each of these steps is described below.

Antibodies specific to GaTx1 are produced by immunizing a non-human mammal (e.g., murine, rodentia, lagomorpha, ovine, porcine, bovine, etc.) with isolated GaTx1. Immunization and hybridoma production with the scorpion venom toxin polypeptide can be accomplished according to conventional methods well known in die art. The immunized animal is an immunocompetent, non-human mammalian host, including murine, rodentia, lagomorpha, ovine, porcine, bovine, etc, is immunized with scorpion venom toxin polypeptide isolated as described above. The choice of a particular host is primarily one of convenience. Immunizations are generally performed in accordance with conventional techniques.

Either monoclonal or polyclonal antibodies, preferably monoclonal antibodies (MAbs), are produced from the immunized animal. Polyclonal antisera may be harvested from serum in accordance with conventional methods after completion of the immunization schedule. For production of MAbs, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Methods for hybridoma production are well known in the art (see, e.g., Antibodies, A Laboratory Manual, Harlow & Lane eds., (1988) Cold Spring Harbor Press).

The antibodies and MAbs can be modified in any of a variety of ways, with the proviso that the modified MAbs retain substantially specific binding to the original antigen (e.g., to the original scorpion venom toxin polypeptide). The ability of such modified antibodies to specifically and sensitively bind their original antigen can be assessed in in vitro assays as described herein (e.g., to assess binding of the modified antibodies to scorpion venom toxin in cytospin preparations, to scorpion venom toxin cell-specific polypeptides in ELISA assays, etc.). Such screening is routine and with the guidance provided herein, within the skill of the ordinarily skilled artisan.

Modified antibodies contemplated by the present invention include those produced using biochemical, chemical, or recombinant DNA techniques. For example, antibody fragments, such as Fv, F(ab')2 and Fab may be prepared from the antibodies of the invention by cleavage of the intact protein, e.g., by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule. Preferably, such antibody fragments retain antigen avidity and/or affinity that is substantially the same as the original antibody from which they are derived.

The subject antibodies may also be produced as a single chain, instead of the normal multimeric structure. Single chain antibodies are described in Jost et al. (1994) J. Biol. Chem. 269:26267 73, and others. DMA sequences encoding the variable region of the heavy chain and the variable region of the light chain are ligated to a spacer encoding at least about four amino acids of small neutral amino acids, including glycine and/or serine. The protein encoded by this fusion allows assembly of a functional variable region that retains the specificity and affinity of the original antibody.

The antibodies may also be humanized. Methods of humanizing antibodies are well known in the art. The humanized antibody may be the product of an animal having transgenic human immunoglobulin (Ig) constant region genes (see for example, WO 90/10077 and WO 90/04036). Alternatively, the antibody of interest may be engineered by recombinant DNA techniques to substitute the $CH_1$, $CH_2$, $CH_3$, hinge domains, and/or the framework residues with the corresponding human sequence (see WO 92/02190). Humanized antibodies are of particular interest for in vivo use in humans.

The antibodies may also be used to produce chimeric antibodies. The use of Ig cDNA for construction of chimeric Ig genes is known in the art (Liu et al. (1.987) Proc. Natl. Acad. Sci. 84:3439; Liu et al. (1987) J. Immunol, 139:3521). mRNA Is isolated from a hybridoma or other cell producing the antibody and used to produce cDNA. The cDNA of interest may be amplified by the polymerase chain reaction using specific primers (U.S. Pat. Nos. 4,683,195 and 4,683,202), Alternatively, a library is made and screened to isolate the sequence of interest. The DNA sequence encoding the variable region, of the antibody is then fused to human constant region sequences. The sequences of human constant regions genes may be found in Kabat et al. (1.991) Sequences of Proteins of Immunological Interest, N.I.H. publication no. 91 3242. Human C region genes are readily available from known clones. The chimeric, humanized antibody is then expressed by conventional methods.

Expression vectors for use in modification of the antibodies of the invention are well known in the art and include plasmids, retroviruses, YACs, EBV derived episomes, and the like. For example, where the scorpion venom toxin polypeptide antibody is to be modified to provide a human antibody heavy and/or light chain constant region, a convenient vector is one that encodes a functionally complete human CH or CL Ig sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell Biol. 3:280), Rous sarcoma virus LTR (Gorman et al. (1982) Proc. Natl. Acad. Sci. 79:6777), and Moloney murine leukemia virus LTR (Grosschedl et al. (1985) Cell 41:885); native Ig promoters, etc.

VII. Kits

The detection methods discussed above can be provided as part of a kit. Thus, one embodiment, provides kits for detecting the presence and/or a level of ABC transporter ligand or ABC transporter ligand-encoding polynucleotides in a biological sample. Procedures using these kits can be performed by clinical laboratories, experimental laboratories, medical practitioners, or private individuals. The kits for detecting a ABC transporter ligand include a moiety that specifically binds scorpion venom polypeptide, including, but not limited to, ABC transporter ligand-specific antibody and an ion channel polypeptide. The kits for detecting a sABC transporter ligand-encoding polynucleotide include a moiety that specifically hybridizes to a ABC transporter ligand-encoding polynucleotide. The kit may optionally provide additional components that are useful in the procedure, including, but not limited to, buffers, developing reagents, labels, reacting surfaces, means for detections, control samples, standards, instructions, and interpretive information.

Pharmaceutical kits for the treatment of scorpion stings, which include one or more containers containing a pharmaceutical composition including a therapeutically effective amount of a GaTx1 polypeptide compound or antibody to a GaTx1 polypeptide. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The disclosure is further defined in the following Examples. It should be understood that these Examples, while indicating preferred embodiments, are given by way of illustration only. From the above discussion and these Examples, one skilled in the art can ascertain the essential characteristics of the various embodiments, and without departing from the spirit and scope thereof can make various changes and modifications to adapt to various usages and conditions.

EXAMPLES

Methods

Oocyte Preparation and Electrophysiology

Figure 10:
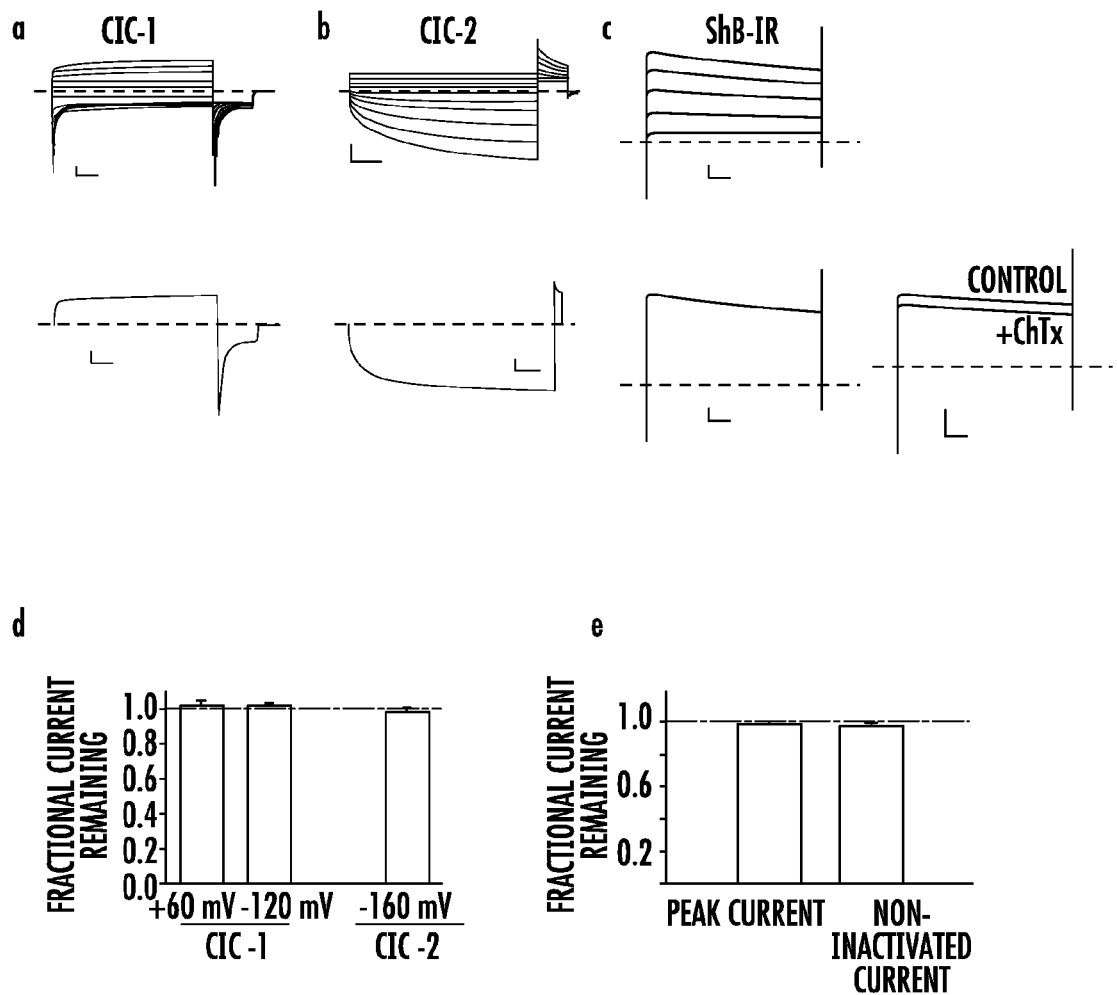

Adult female *Xenopus* were obtained from *Xenopus* One (Ann Arbor, Mich.). Methods for oocyte preparation have been previously described, cRNAs were prepared from high expression vectors encoding WT-CFTR (pGEMHE-WT) or Flag-cut-ΔR-CFTR (pGEMHE-Flag3-633 plus pGEMHE-837-1480). Oocytes were injected with 5-25 ng cRNA for single channel experiments, or 25-100 ng cRNA for macropatch experiments. Methods for electrophysiological recording of CFTR single channel and macropatch currents, and analysis, have been described previously. Briefly, all fractions were tested using either excised/inside-out macropatches or single channel patches. For all experiments except those depicted in FIG. 6 and FIG. 10, VM=−80 mV. The single channel record in FIG. 6 was performed at VM=−100 mV. For macropatch experiments, solutions containing 1 mM MgATP, no MgATP, fraction (or venom), or MgATP plus traction (or venom) were perfused onto the intracellular face of the channel using a last perfusion system (Warner instruments, model SF-77B), as previously described. All single channel recordings of WT-CFTR were performed in the continuous presence of 1 mM MgATP and 50 U/mL PKA. Multi-channel patch experiments with Flag-cut-ΔR-CFTR in FIG. 7 were performed in the continuous presence of 0.2 or 1 mM MgATP. Human ClC-1 and rabbit ClC-2 were expressed in oocytes and studied using two-electrode trade voltage clamp, as previously described. For experiments with ShB-IR, oocytes were injected with 0.06-1 ng cRNA. Leak currents were subtracted using a P/4 protocol; corrected traces are shown. For all figures including electrophysiological recordings, the thick horizontal dashed line indicates die closed current level.

Statistics

Results are reported as mean±S.E. for n observations. Statistical Significance was assessed using paired and unpaired Student's t-tests, Differences were considered statistically significant when $p<0.05$.

Example 1

Inhibition of CFTR by Scorpion Venom

Venom from the scorpion *L. quinquestriatus hebraeus* was obtained from Latoxan (France) and processed as previously described. Briefly, venom was resuspended in recording solution, disrupted by a tissue grinder, and centrifuged in order to separate the mucous component. The supernatant was then passed through a 10 kDa MW cut-off spin filter to remove high molecular weight components, resulting in "Lqh-pf venom". Venom or traction concentrations are stated as equivalent to venom dry weight before processing. For toxin separation by chromatography, Lqh-pf venom was resuspended at a concentration of 5 mg/mL equivalent.

A summary of the inhibitory activity of partially-fractionated venom ("Lqh-pf venom") on CFTR channels in both macropatches and single-channel patches pulled from *Xenopus* oocytes is shown in FIG. 1b-d. Lqh-pf venom contains all components <10 kDa in size. Rapid application of 0.1 mg/mL Lqh-pf venom (dilution equivalent to this concentration of unfractionated venom based upon venom dry weight) to closed wildtype (WT)-CFTR channels resulted in inhibition of macroscopic current by ~25% at Vm=−80 mV, as previously described. Venom was applied to phosphorylated CFTR channels that had been allowed to close upon removal of cytosolic ATP. When ATP was returned to the bath, the resulting current density was reduced. Similar results were seen when Lqh-pf venom was applied to Flag-cut-ΔR-CFTR channels (FIG. 1a right, FIG. 1b right), which lack the regulatory R domain and therefore do not require PKA-mediated phosphorylation, suggesting that the decrease in current observed in WT-CFTR is due to venom-induced inhibition rather than channel rundown mediated by membrane-bound phosphatases. When the inhibitory activity was further characterized at the single channel level, the active components) of venom inhibited channel activity in a complex manner. Application of Lqh-pf venom onto single WT-CFTR channels in excised patches resulted in a substantial decrease in channel open probability ($P_o$). As shown in FIG. 1c, venom application led to complete knockout of some channels for tens of seconds to minutes by binding to the channels in the interburst closed state. Venom application also resulted in the introduction of toxin-induced intraburst blocked states in those channels that were able to open (FIG. 1d); these events were previously shown to arise from venom binding during brief intraburst closings, leading to the prolongation of those intraburst closed states. These results suggest that Lqh-pf venom may contain two separate toxins that bind to CFTR during different phases of the gating cycle, or one toxin that Inhibits in two different ways.

Example 2

Separation of Active Components in Venom

Figure 2:
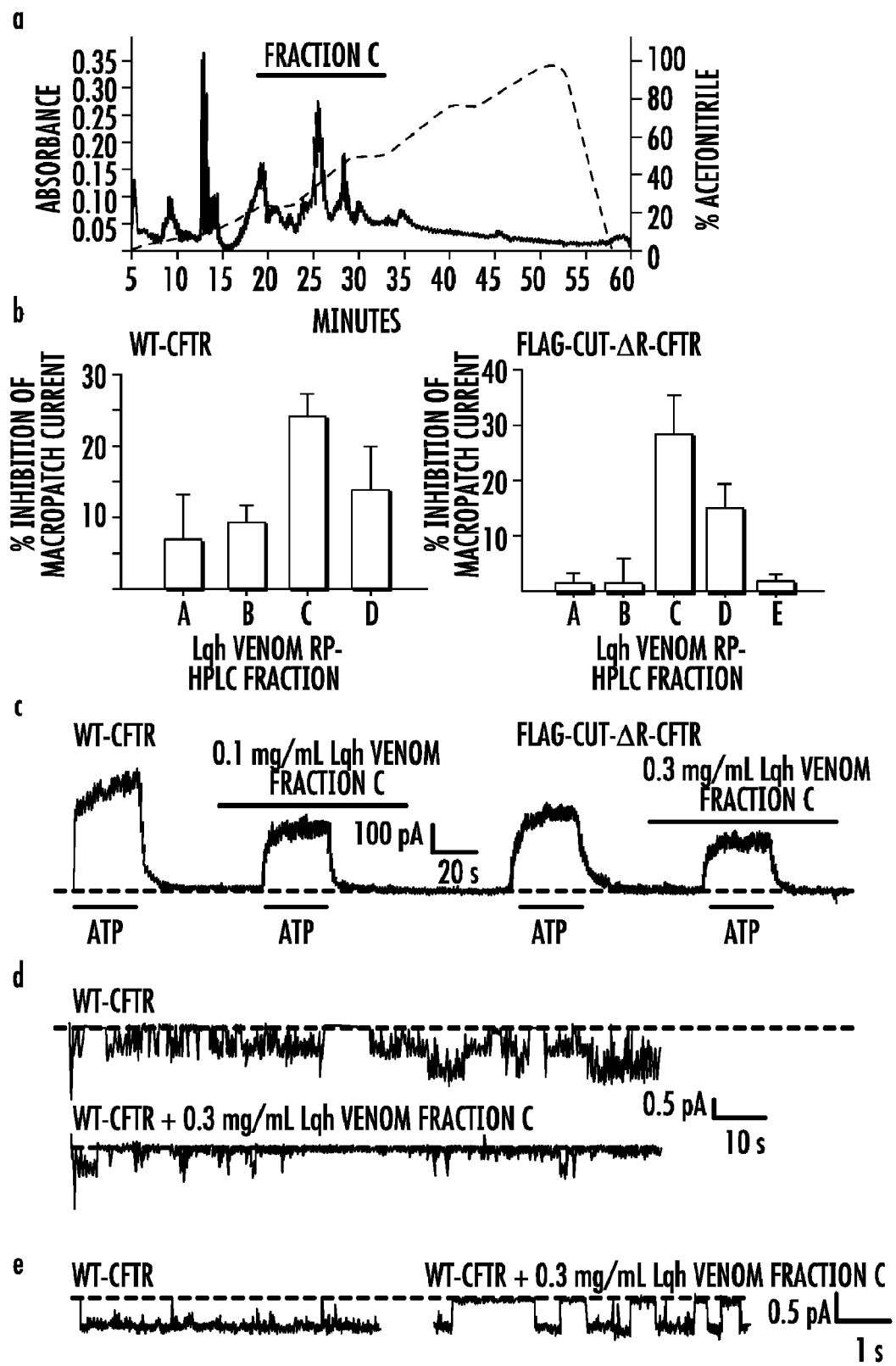
FIG. 2: inhibition of CFTR by Lqh-pf venom fraction C. (a) Representative RP-HPLC chromatogram of Lqh-pf venom. Fractions A-E of the eluate were collected during successive ten minute intervals, (b) Summary data of average percent inhibition of WT- or Flag-cut-ΔR-CFTR macropatch currents by venom fractions at 0.1 or 0.3 mg/mL equivalent, respectively. Error bars show mean±S.E. for n=3-4 observations at each condition. Fraction C showed the highest activity. (c) Representative macropatch currents of WT- and Flag-cut-ΔR-CFTR in die absence or presence of Lqh venom fraction C. (d) Representative single channel traces of WT-CFTR in the absence and presence of Lqh venom fraction C. Fraction C inhibits WT-CFTR by inducing long interburst closures. (e) Expanded WT-CFTR bursts in the absence and presence of Lqh venom fraction C. Note that fraction C also introduces intraburst closures that are not observed in the absence of the fraction. Thus, Lqh venom fraction C fully recapitulates the activity of Lqh-pf venom.

Lqh-pf venom was fractionated by means of reversed-phase HPLC (RP-HPLC) (FIG. 2a). Components of Lqh-pf venom were separated based on hydrophobicity, using a Waters 1525 binary HPLC coupled to a Waters 2487 dual wavelength absorbance detector, with a Zorbax 300SB-C3 silica column (4.6×250 mm, 5 µm, 300 Å pore size), and a gradient of water and acetonitrile. Size exclusion-chromatography used a 1.4 cm×80 cm chromatography column (Bio-Rad) packed with Sephadex G50 Superfine (Sigma); toxins were eluted using a buffer containing 50 mM Tris-HCl and 100 mM KCl (pH 7.5). Dextran, cytochrome C, and vitamin B were used as standards during column equilibration. All fractions collected via RP-HPLC or size exclusion chromatography were dried under vacuum, then resuspended in the appropriate recording solution, and stored at ~80° C. until use. For all chromatograms, the solid line indicates absorbance at 220 nm. The dashed line in RP-HPLC chromatograms indicates the elution gradient.

Elution fractions were examined for activity against WT-CFTR in excised inside-out macropatches (FIG. 2b, FIG. 2c). The fraction collected from 20-30 minutes (fraction "C") resulted in 23.7±3.4% (n=3) inhibition of macroscopic current at a dilution equivalent to 0.1 mg/mL venom; however, fractions-collected at other times also had some effect. The wide ranging apparent inhibitory activity suggested by these data may be due to a small degree of dephosphorylation-mediated rundown of WT-CFTR. channels. Therefore, similar experiments using Flag-cut-ΔR-CFTR expressed in excised, inside-out macropatches were performed (FIG. 2b, FIG. 2c (right)). Fraction C resulted in 27.9±7.2% (n=4) inhibition of macroscopic Flag-cut-ΔR-CFTR current; some activity spilled over into fraction D.

To determine the mechanism of inhibition induced by venom fraction C, excised, inside-out patch recordings of single CFTR channels were studied in the absence and presence of fraction C (FIG., 2d). Exposure to fraction C resulted in a decrease in $P_o$, due to a decrease in channel opening rate associated with an apparent prolongation of the interburst closed duration. In addition, expanded displays of single open channel bursts indicated that application of fraction C also led to the introduction of intraburst closings (FIG. 2e). These results suggested that fraction C contains both of the activities previously described for venom.

Figure 3:
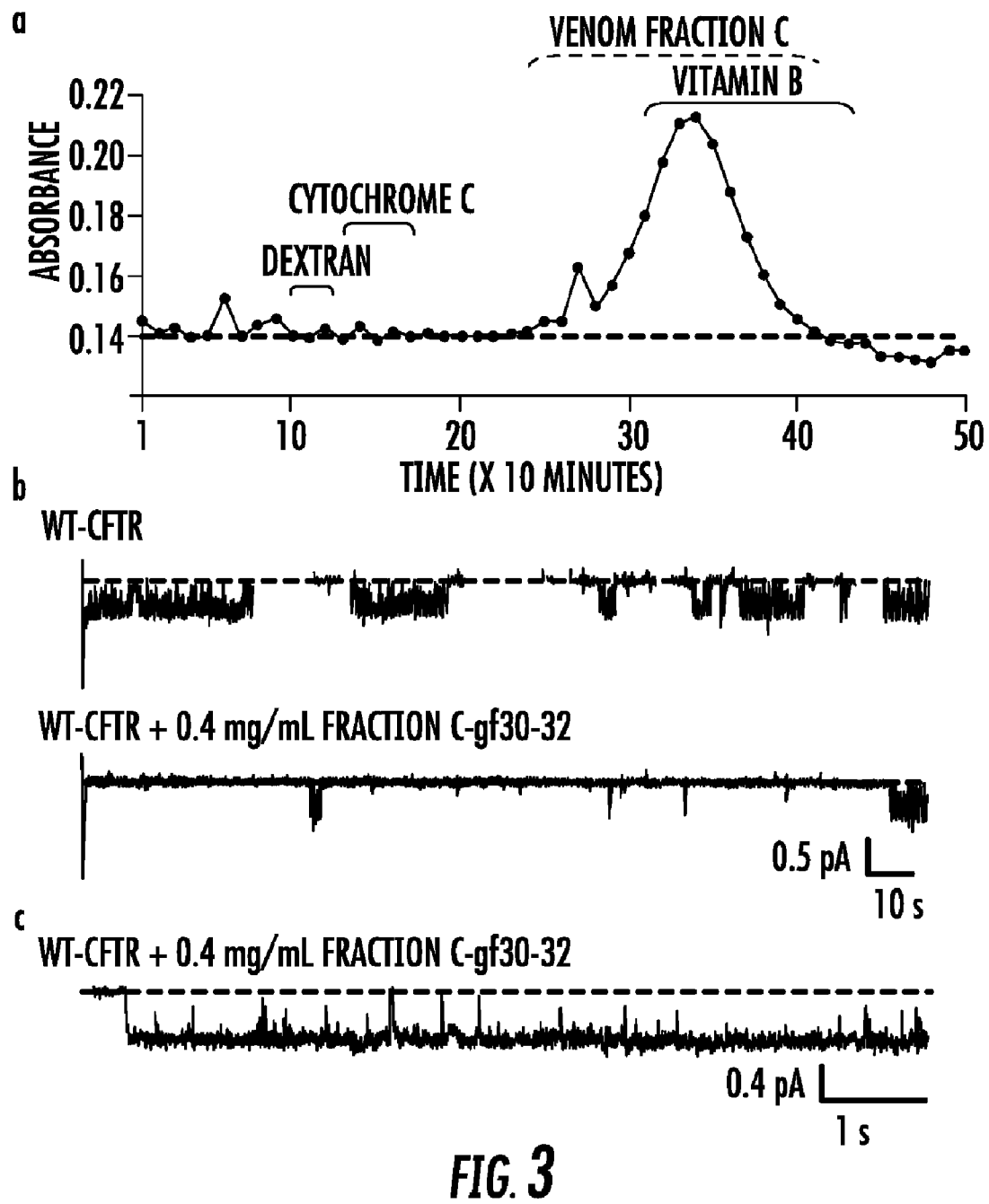
FIG. 3: Fractionation of venom by size exclusion chromatography. (a) Representative chromatogram of fraction C applied to a size exclusion column. Fractions were collected every 10 minutes and pooled into 30 minute fractions. The dashed line indicates baseline absorbance of elution buffer. Solid brackets indicate elution times for the indicated molecular weight standards in calibration runs (dextrans, 2 million Da; cytochrome C, 12,384 Da; vitamin B, 1,255 Da). (b) Representative single channel recording in the absence and presence of venom fraction C-gf30-32. (c) Expanded single channel burst of WT-CFTR in the presence of the active fraction showing that the component of venom causing intraburst inhibition is no longer present.
Figure 4:
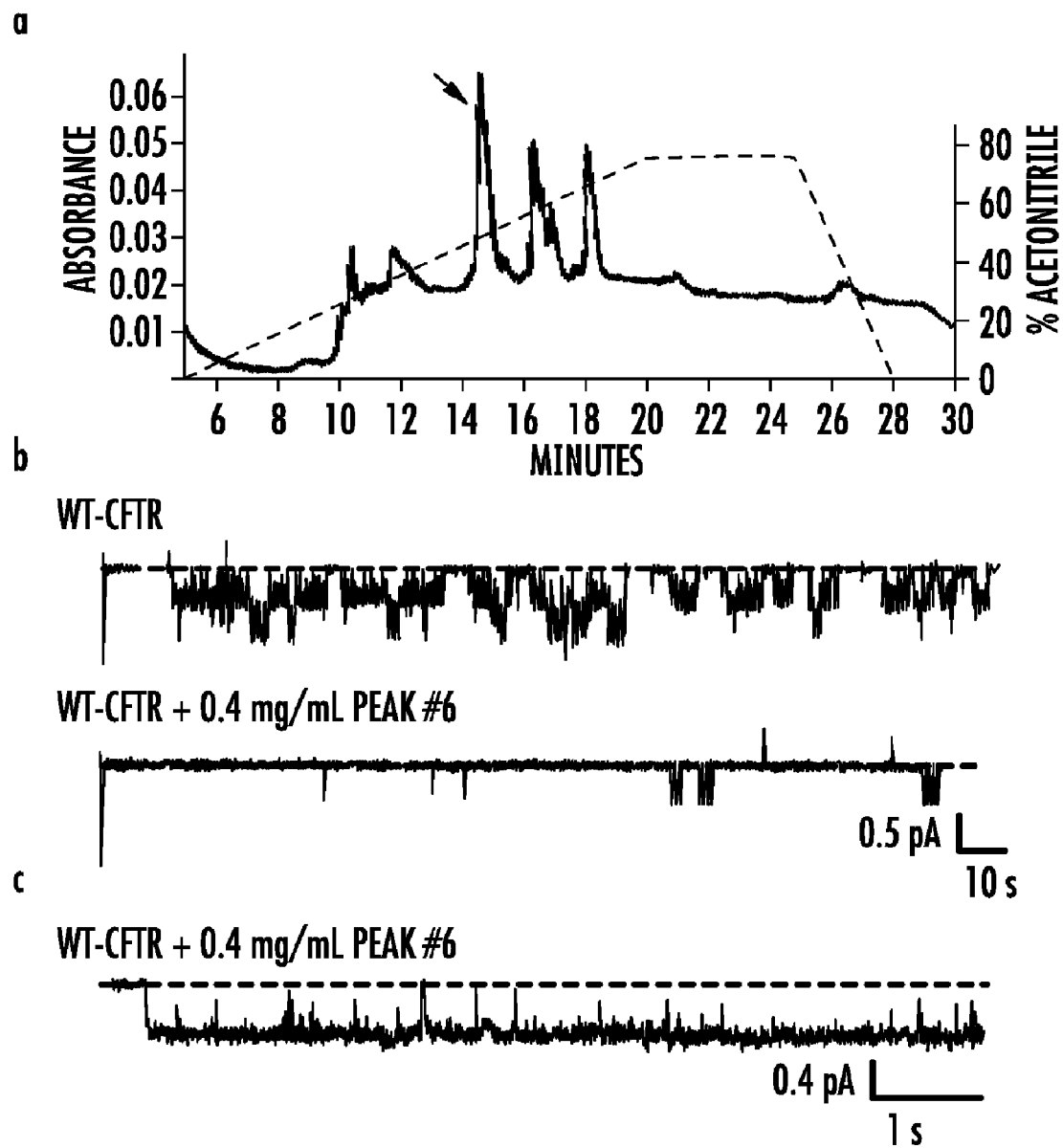
FIG. 4: Isolation of the active peak, (a) Representative RP-HPLC chromatogram of fraction C-gf30-32. Individual peaks were collected and tested for activity as in FIG. 1. The arrow indicates the active peak, peak #6. (b) Representative single channel trace in the absence and presence of peak #6. The isolated toxin Inhibits CFTR by increasing the interburst closed duration. (c) Expanded section of trace showing that peak #6 does not induce intraburst inhibition.

Sequential purification using gel-filtration .chromatography (FIG. 3a) and RP-HPLC (FIG. 4a) resulted in the isolation of a single peptide whose biological activity was sufficient to recapitulate the interburst inhibitory activity of crude venom. The size-exclusion fractions collected from 300-336 minutes (fraction C-gf30-32) resulted In significant. Inhibition of WT-CFTR current at the single-channel level. Recordings of WT-CFTR in the absence and presence of fraction C-gf30-32 suggested that the fraction inhibited CFTR by inducing long-lived interburst closings (FIG. 3b) without affecting apparent burst duration. However, the venom-induced intraburst closings that were apparent during inhibition by fraction C were notably absent (FIG. 3c). These findings suggest that at least two toxins active at CFTR are contained in Lqh-pf venom and that the toxin responsible for inducing intraburst blocked states was not contained in fraction C-gf30-32.

Fraction C-gf30-32 was then further separated by RP-HPLC (FIG. 4a). The chromatographic peak collected ~15 minutes into the run, peak #6, was found to inhibit WT-CFTR single channels (FIG. 4b). None of the other collected peaks had any inhibitory activity (data not shown). Single-channel recordings of WT-CFTR activity in the absence and presence of peak #6 indicated that the fraction inhibited CFTR by inducing long-lived interburst closings (FIG. 4b). In contrast, die venom-induced intraburst closings were not present (FIG. 4c). Peak #6-caused a 58.2±11.3% decrease in $P_o$ from 0.19±0.06 in control conditions to 0.06±0.004 (n=3) in presence of peak #6. From these results we concluded that peak #6 contained a peptide ligand which inhibited WT-CFTR.

Example 3

Characterization of the Isolated Peptide Ligand

Initial characterization of the active peptide contained in peak #6 was accomplished by subjecting a small aliquot of the material to MALDI-TOF analysis. A single peptide was identified with a molecular mass of 3,674.6 Da (FIG. 5a), Additional, less/abundant peaks with similar mass were also identified that likely represent different oxidative states of the same toxin; a doubly charged species also was observed (m/z=1,838.8 Da). The peptide in peak #6 then was subjected to automated amino terminal sequencing following destruction of all putative disulfide bridges by reduction with DTT and alkylation of free cysteines by iodoacetamide. The reduction and alkylation of the native toxin resulted in an increase in molecular mass to 4,138.5 Da as determined by MALDI-TOF, which is in agreement with the modification of eight cysteines; expected mass=4,138.6 Da (Table 2).

TABLE 2

Mass spectrometric analysis of native and synthetic GaTx1

|  | Intact Monoisotopic MH+ Mass | Modified Monoisotopic MH+ Mass* |
|---|---|---|
| Native GaTx1 | | |
| Observed | 3674.7 | 4138.5 |
| Theoretical | 3674.5 | 4138.6 |
| Synthetic GaTx1 | | |
| Linear | 3682.1 | |
| Cyclized GaTx1 | 3674.2 | |

*Modified molecular mass represents the mass of the native toxin that has been reduced with DTT, and modified with iodoacetamide.

The toxin isolated from venom, or the reduced/carboxamidomethyl-modified toxin, was purified by microbore RP-HPLC (Applied Biosystems model 140A/785A system) on a Zorbax SB-C18 silica column (1×150 mm, 5 µm, 300 Å pore size) equilibrated in 0.1% aqueous TFA and eluted at 25° C. using a linear gradient of acetonitrile in 0.08% aqueous TFA. The toxin was eluted as a dominant peak absorbing at 214 nm which was collected and further analyzed.

RP-HPLC fractions of either the native or reduced/carboxamidomethyl-modified intact toxin were sequenced. The peptides were loaded onto a Biobrene-coated and pre-cycled glass fiber filter disc and sequenced using a model cLC-Procise sequencer/PTH Analyzer (Applied Biosystems) using the manufacturer's pulse-liquid Edman degradation chemistry cycles. To further confirm the sequence data obtained by N-terminal sequence analysis, an aliquot of the reduced/carboxamidomethyl-modified toxin was digested with Lys-C protease which is specific for Lys-Xxx peptide bonds. The digest was separated by RP-HPLC and the resulting three fractions were manually collected and subjected to Edman sequencing as above. The sequences of the three fragments corresponded to: (1) N-term.: CGPCFTTDHQMEQK (residues 1-14 of SEQ ID NO:1); (2) Middle: CAECCGGIGK (residues 15-24 of SEQ ID NO:1); and (3) C-term.: CYGPQCLCNRamide (SEQ ID NO:38). The C-terminal fragment was further analyzed by ESI-MS/MS, yielding a molecular ion of 1,325.5 Da, which agrees with the calculated mass of this fragment based on sequence assuming a C-terminal amide. The ESI-MS/MS data also confirmed the presence of three carboxamidomethyl-Cys residues in this fragment. The primary sequence was determined to be: $^1$CGPCFTTDHQMEQKCAECCGGIGKCYG-PQCLCNR$^{34}$ (SEQ ID NO:1), including C-terminal amidation as the only post-translational modification other than formation of disulfide bridges.

Peptide monoisotopic masses (Table 2) were obtained by MALDI-TOF MS analysis using the Applied Biosystems model 4700 Proteomics Analyzer (MALDI-TOF/TOF) system operated in the reflector mode. The calculated mass of the isolated toxin based upon primary sequence and assuming post-translational C-terminal amidation was in close agreement with the mass determined by MS; these results suggest that the toxin does not include bound metal ions. To confirm the primary sequence, an aliquot of the reduced/carboxamidomethyl-modified toxin was digested with Lys-C protease and analyzed by Edman degradation and ESI-MS/MS, resulting in the same primary sequence data. The same toxin has been purified from three different batches of scorpion venom.

Figure 5:
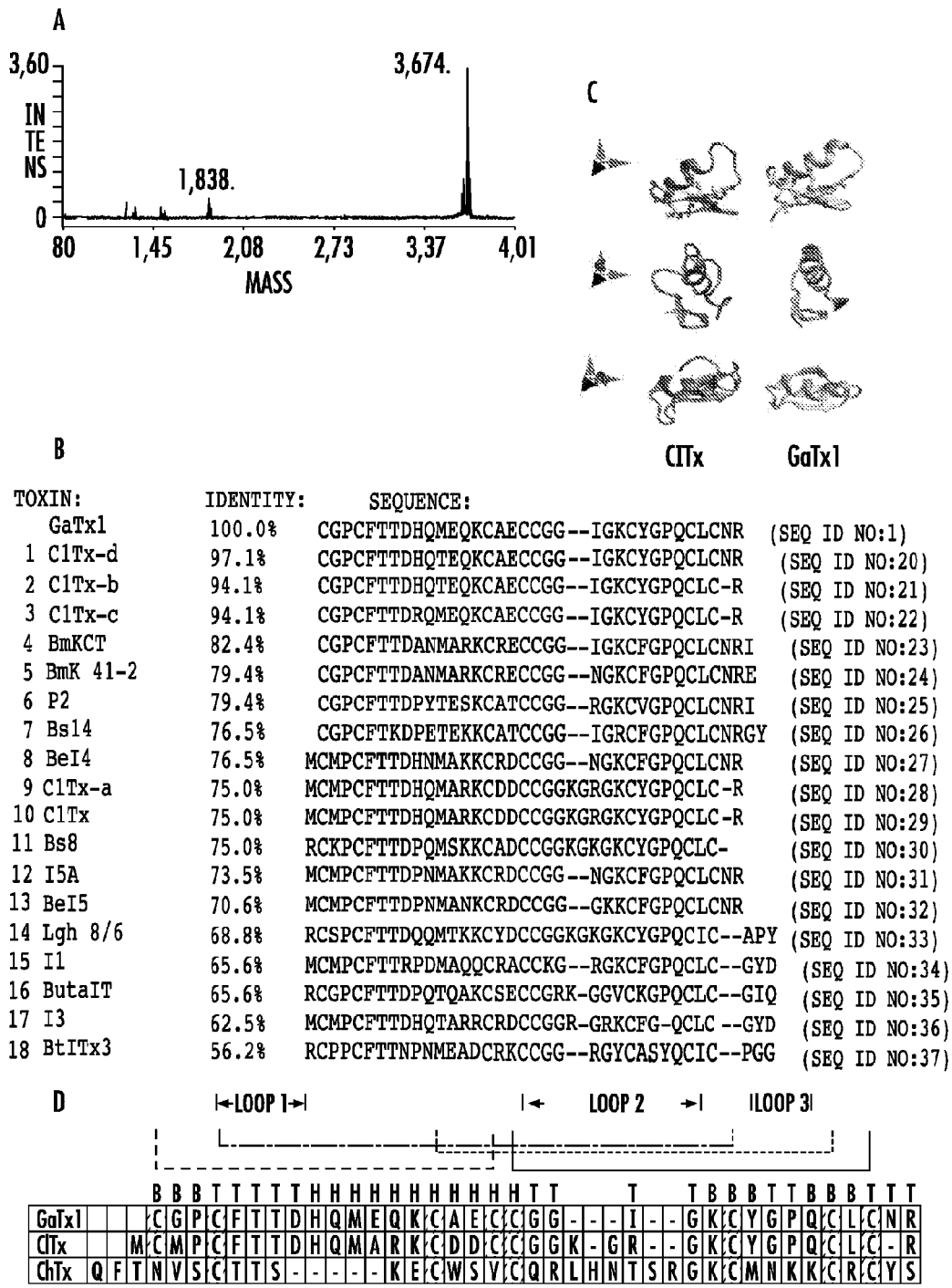
FIG. 5: Proteomic characterization of GaTx1. (a) MALDI-MS spectrum of peak #6, showing a prominent mass of ~3.7 kDa. (b) Alignment of the GaTx1 sequence with other scorpion toxins shows that GaTx1 is a novel peptide. (c) Comparison of the ClTx NMR structure (left) and the GaTx1 homology model (right), in three orientations. Disulfide bridges are shown in the upper panels. (d) Sequence alignment of GaTx1 (SEQ ID NO:1) with the sequences of chlorotoxin (ClTx) (SEQ ID NO:29) and charybdotoxin (ChTx) (SEQ ID NO:39). Predicted secondary structure is indicated above the sequences while disulfide bridge linkage between conserved cysteines is indicated below. The dashed line indicates the disulfide bridge absent in ChTx.

Comparisons of the primary sequence with those of other known or putative peptide ligands suggested that the isolated toxin, which is named GaTx1, is novel, with ClTx-d as its closest relative (FIG. 5b). ClTx-d is not known to inhibit any ion channel; indeed, the sequences of ClTx-b, -c, and -d are speculative, being predicted from the sequences of cDNAs cloned from scorpion venom gland. GaTx1 bears 75% sequence identity to ClTx, but is smaller by ~400 Da. The calculated pI values for GaTx1 and ClTx are 6.71 and 8.13, respectively. The primary sequence of GaTx1, the molecular mass, and the inferred presence of four disulfide bridges between conserved cysteines place this toxin in the family of short-chain insectotoxins active at $K^+$ channels and putative toxins active at $Cl^-$ channels.

A homology model of GaTx1 was created based on the known NMR structures of ClTx and insectotoxin 5A (I5A) (sequences 10 and 12 in FIG. 5b). The homology model of GaTx1 was created using Modeller 8.2, with the NMR structures of chlorotoxin and insectotoxin I5A providing template structures. The GaTx1 homology model was then subjected to a 5 ps, 2500 step energy minimization in a solvated environment using NAMDv2 with the charmm22 force field. Disulfide bridges were patched in order to ensure that disulfide bonds remained intact during energy minimization. All graphics were rendered from VMD 1.8.4 software in combination with POV-Ray 3.6.

FIG. 5c shows the NMR structure of ClTx and the homology model of GaTx1, in three orientations. The two structures are quite similar in shape and secondary structure, although GaTx1 has three regions of anti-parallel β-strand compared to two in ClTx; the extra strand is at the immediate N-terminus. The I5A toxin structure (not shown) includes three β-strands and a longer α-helix compared to ClTx. GaTx1 is also somewhat more compact than ClTx, partly due to the insertion of two amino acids C-terminal to the α-helix In ClTx, and due to the lack of defined secondary structure in the first loop Of ClTx, resulting in a bulge of relatively disordered sequence at the N-terminal end of the α-helix in ClTx. FIG. 5d identifies the borders of regions of predicted secondary structure for GaTx1, and compares the GaTx1 sequence with that of ClTx and charybdotoxin (ChTx). While the most striking primary structure differences between short-chain insectotoxins (including all three of these) and the longer toxins that inhibit $Na^+$ channels and $Ca^{2+}$ channels 10 are the lengths of loops 2 and 3, the major differences between GaTx1 (which inhibits CFTR) and ClTx (which does not) are in the α-helix.

Example 4

Kinetics of Inhibition of CFTR by GaTx1

Figure 6:
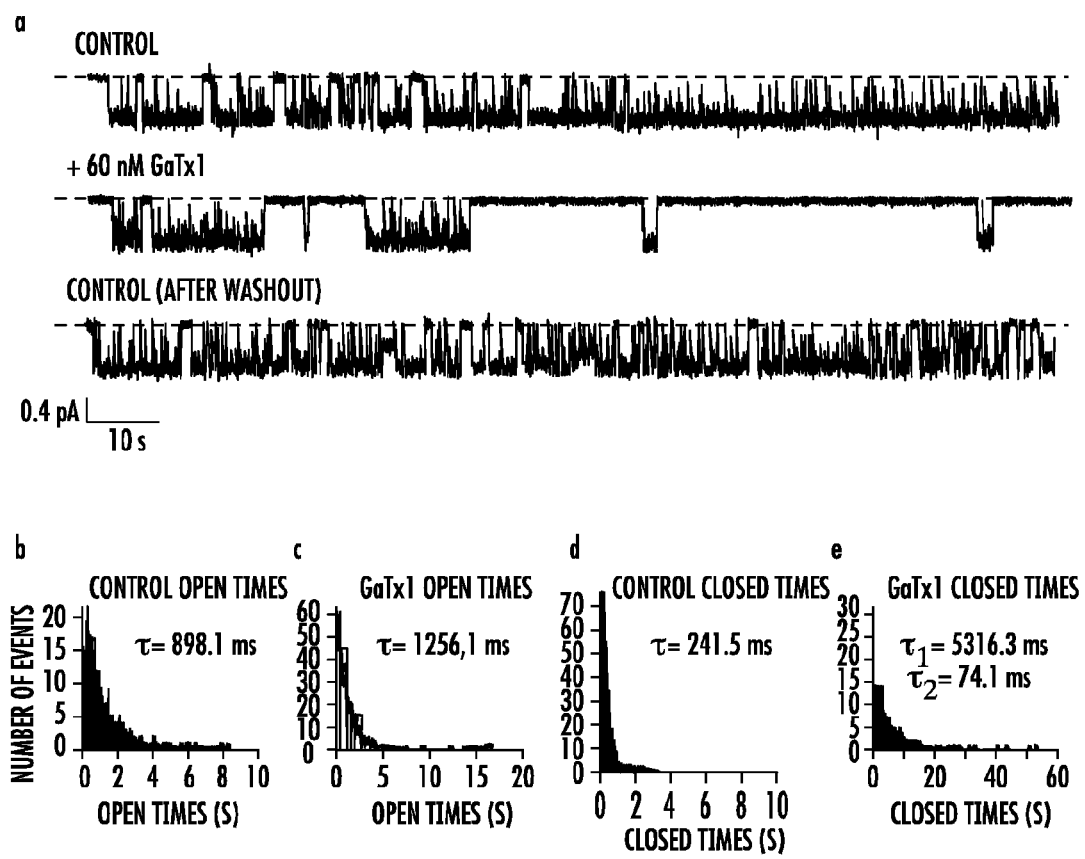
FIG. 6: Native GaTx1 inhibits CFTR by increasing the interburst closed duration. (a) Representative single channel traces of WT-CFTR in the absence and presence of 0.1 mg/mL venom equivalent GaTx1; this dilution was determined by amino acid analysis to provide 60 nM native GaTx1. Open probability was significantly reduced in the presence of toxin, (b-e) Burst analysis of CFTR open durations in the absence (b) and presence (c) of GaTx1, and CFTR closed durations in the absence (d) and presence (e) of GaTx1. For this analysis, the record after toxin washout was used as control, to account for any potential, loss of channel activity due to rundown. Toxin increased the interburst closed time, but had no significant effect on CFTR open duration. The closed duration histogram in the presence of toxin was fit best with the sum of two exponential functions with time-constants $\tau_1$=5316.3 ms (fractional amplitude=19.8%) and $\tau_2$=74.1 ms (fractional amplitude=80.2%).
Figure 7:
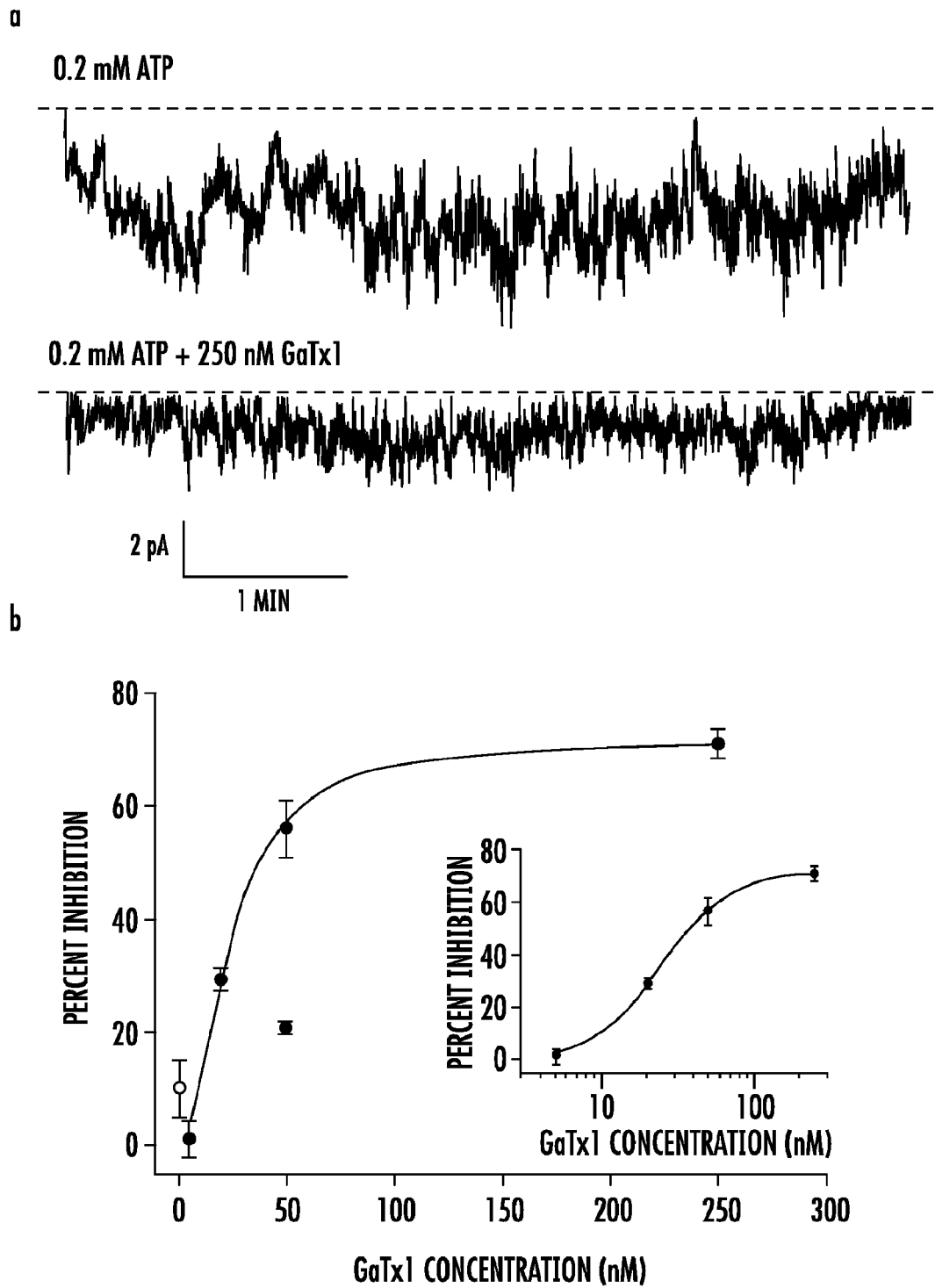
FIG. 7: Synthetic GaTx1 inhibits CFTR with high affinity. (a) Representative multi-channel trace of Flag-cut-ΔR-CFTR in the absence and presence of 250 nM synthetic GaTx1, with continual exposure to 0.2 mM ATP. (b) Dose-response curve calculated from window currents measured at 5, 20, 50, and 250 nM synthetic GaTx1. Each filled symbol and error bar represents calculation of window current from a single patch at that concentration where macroscopic current was calculated within five randomly-chosen 3-minute segments each under control and experimental conditions. The open circle represents apparent inhibition calculated from sequential exposures to solution containing 0.2 mM ATP without toxin, as negative control; these data are not significantly different from zero. The dose-response curve was fit with a 3-parameter Hill function giving KD=24.9 nM, Vmax=71.5% inhibition, and Hill coefficient=1.95 (correlation coefficient r2=0.998). Filled triangle shows data from an experiment with 50 nM GaTx1 in presence of 1 mM ATP.

FIG. 6 shows data from a single-channel recording of WT-CFTR in the absence of toxin (upper and lower traces) and in the presence of 60 nM GaTx1 (middle trace), indicating reversible inhibition. Consistent with the data shown in FIGS. 1-4, exposure of single CFTR channels to GaTx1 in an inside-out patch led to the introduction of long closed/blocked states without affecting the duration of the open states. Toxin-induced closed durations are very long; the mean toxin-Induced closed duration in this experiment was >5 seconds. However, evident in the dwell-time distribution (FIG. 6e) are toxin-induced closed states that lasted nearly a minute. Similarly long toxin- or venom-induced closed durations are evident in FIGS. 1-4. Hence, GaTx1 interacts with CFTR ~1.000-fold longer than most known blockers. This intimate interaction means that GaTx1 will be a very informative probe of CFTR structure.

Example 5

Synthetic GaTx1 Selectively Inhibits CFTR

Figure 8:
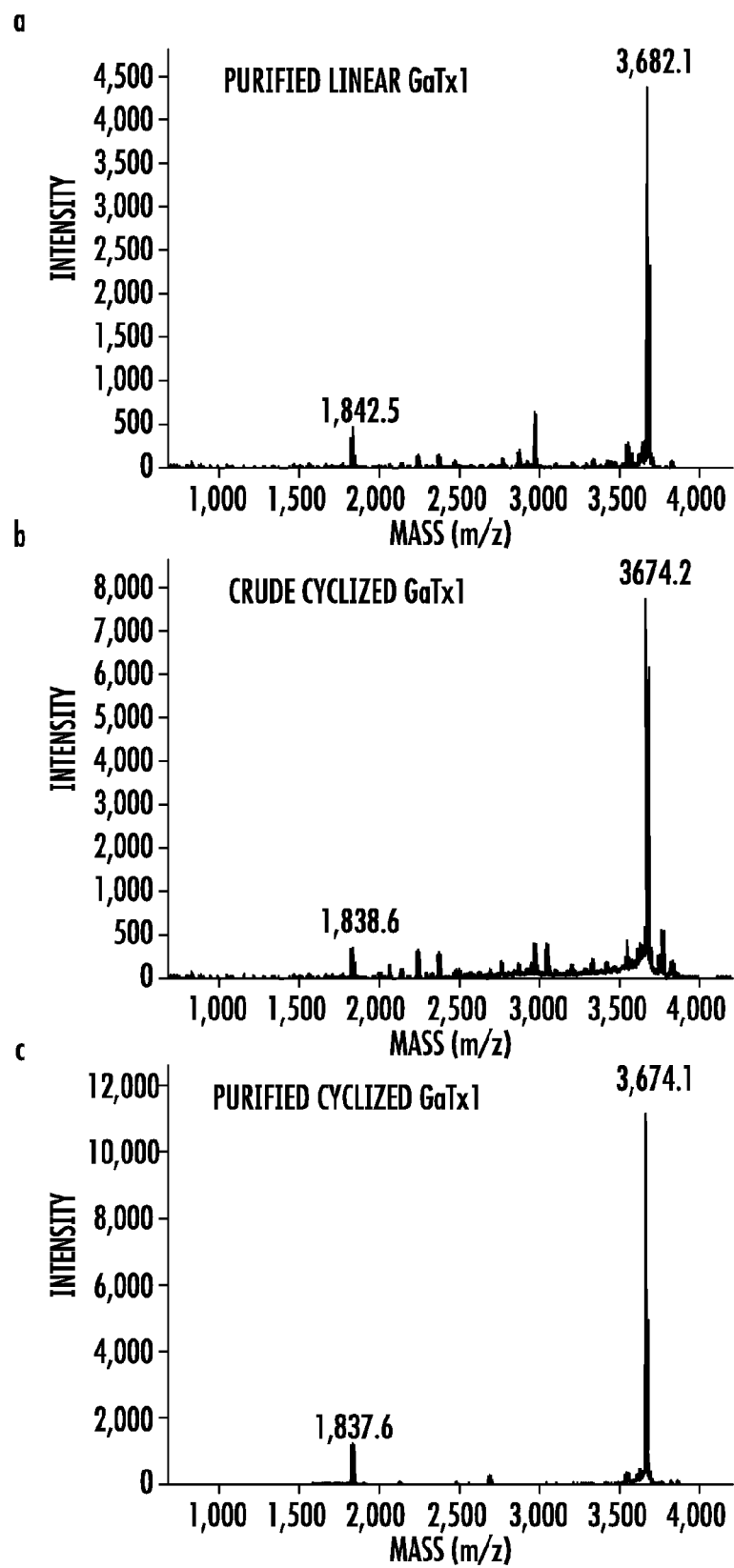
FIG. 8: MALDI-MS spectra of synthetic forms-of GaTx1. (a) GaTx1 was synthesized as described in Methods and subjected to MALDI-MS. Prior to cyclization, the linear peptide showed a mass of 3,682.1 Da, and also displayed a doubly charged state at m/z=1,842.5. (b) MALDI-MS of crude cyclized GaTx1 showed a major component at m/z=3,674.2, as well as a doubly charged state at m/z=1,838.6. (c) After RP-HPLC purification of the dominant component of the cyclized peptide, the major-peak ex cide, an "effective amount" is that amount necessary to kill the insect or pest, or otherwise effect the behavior of the insect or pest in such a way that it no longer performs or causes undesired events or activities, e.g. consume or damage plants.

To confirm that the inhibitory activity in venom could be ascribed to the sequenced toxin, and did not arise from a contaminant, GaTx1 was prepared by solid-phase chemistry. The general methods for peptide synthesis and purification, and disulfide bond formation, have been described previously. In brief, linear peptides were produced by solid phase synthesis using 9-fluorenylmethoxycarbonyl (Fmoc) chemistry. Coupling of Fmoc amino acids was performed using the HBTU/HOBT/DIPEA method on an Applied Biosystems 431A synthesizer. The purified linear peptide was subjected to oxidative cyclization under equilibrating conditions in order to promote formation of the most stable disulfide bridges, with the reaction being monitored by analytical HPLC Cyclized peptide was isolated from the acidified reaction mixture by reversed phase extraction, was purified by HPLC, and was characterized by MALDI-MS for molecular weight determination (FIG. 8) and by analytical HPLC (FIG. 9) for comparison with the native toxin.

Figure 9:
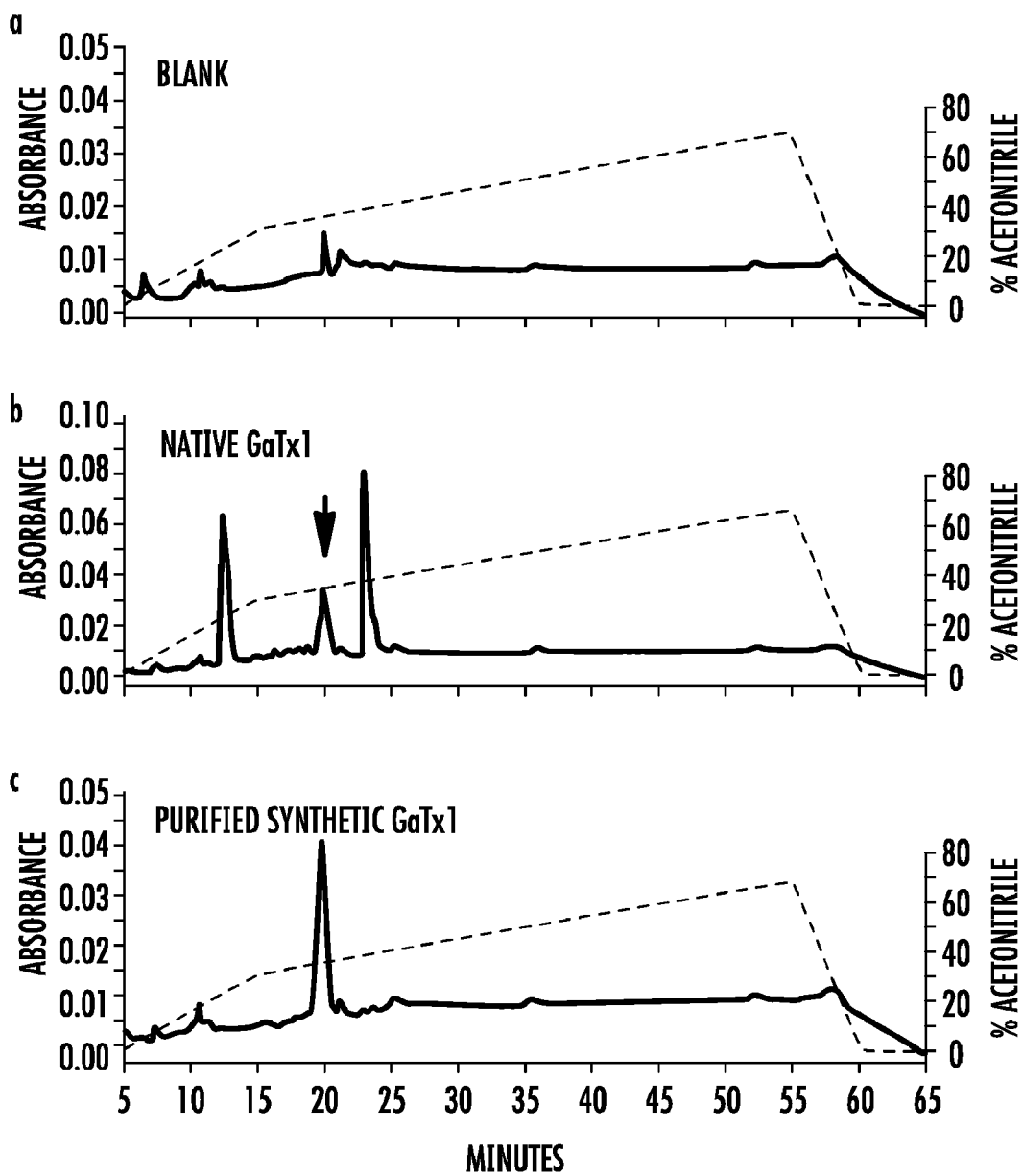

After purification by HPLC, MS analysis indicated that the synthetic linear peptide has a mass in agreement with the theoretical mass for the linear form (i.e., all disulfides reduced to sulfhydryls) of the native toxin (Table 2). The linear peptide was subjected to oxidative cyclization and refolding was performed over three days under equilibrating conditions, in order to promote the formation of the most stable disulfide bridges. The mass of the folded synthetic peptide differed from, the observed mass of the native toxin isolated from venom by only 0.5 a.m.u. (FIG. 8); in RP-HPLC experiments, folded synthetic toxin co-eluted with the native toxin (FIG. 9).

Multichannel patch recordings from oocytes expressing Flag-cut-ΔR-CFTR were used to test for activity of synthetic GaTx1 (FIG. 7a), taking advantage of the insensitivity of this CFTR variant to dephosphorylation-mediated rundown; Flag-cut-ΔR-CFTR is inhibited by venom to a similar degree as WT-CFTR (FIG. 1b). Because GaTx1 binds to channels in the closed state, intracellular solution containing only 0.2 mM ATP was used, which leads to reduced open probability, thus increasing the likelihood of a toxin binding event. FIG. 7b shows a dose-response curve for inhibition of Flag-cut-ΔR-CFTR under these conditions. The data were fit with a 3-parameter Hill function providing a $K_D$ of 24.9 nM and Hill coefficient of 1.95. Maximum inhibition over this concentration range, and in the continual presence of 0.2 mM ATP, was 71.5%. Previous experiments indicated that venom was more effective when applied to CFTR channels in the absence of ATP, leading to strong state-dependence of action. The apparent potency for toxin-mediated inhibition of channel activity would be very protocol dependent; under conditions that increase $P_o$, the apparent magnitude of inhibition should be reduced. As shown in FIG. 7b, 50 nM GaTx1 led to 56.2±5.0% inhibition of Flag-cut-ΔR-CFTR in the presence of 0.2 mM ATP, but only 20.4±0.5% inhibition in the presence of 1 mM ATP (p=0.001). The observation that toxin efficacy depends upon [ATP], combined with a Hill coefficient near 2, suggests that GaTx1 may inhibit CFTR by interacting with the nucleotide-binding domains (NBDs).

To verify the specificity of GaTx1-mediated inhibition, the ability of the toxin to inhibit ClC-1 and ClC-2 channels expressed in oocytes was tested and studied using two-electrode voltage clamp (FIG. 10a, FIG. 10b). Our previous work showed that fraction C or Lqh-pf venom did not inhibit oocyte endogenous $Ca^{2+}$-activated Cl⁻ channels, or ClC-0 or ClC-1 voltage-gated Cl– channels; Lqh-pf venom does contain a separate toxin that inhibits ClC-2 channels, although this is not a component of fraction C. For ClC-1, fractional current remaining at +60 and –0.120 mV in the presence of 60 nM synthetic GaTx1 was 1.02±0.03 and 1.02±0.02, respectively. For ClC-2, fractional time-dependent current remaining at the end of a long pulse to –160 mV was 0.98±0.03 in the presence of 60 nM GaTx1. These data suggest that the GaTx1 toxin does not inhibit either ClC-1 or ClC-2 voltage-gated chloride channels at a concentration at which it effectively inhibits CFTR. GaTx1 bears distant homology to the very well-known charybdotoxin (ChTx) which inhibits a wide variety of voltage-gated and $Ca^{2+}$-activated $K^+$ channels (FIG. 5d). Whether GaTx1 crosses over from Cl⁻ channel to $K^+$ channel targets was determined by assaying for effects on $K^+$ channel currents mediated by Shaker Kv1.1 channels expressed in oocytes. For these experiments, the ShB variant was used with inactivation-removed (ShB-IR). As shown in FIG. 10c, GaTx1 had no effect on ShB-IR $K^+$ currents at a toxin concentration that effectively inhibits CFTR. As a positive control, FIG. 10c shows 15% inhibition of ShB-IR currents by 24 nM recombinant ChTx. This amount of inhibition is consistent with the reported $K_i$ for ChTx-mediated inhibition of Shaker channels of ~200 nM.

Previous studies indicated that a toxin or toxins contained in Lqh venom preferentially inhibits CFTR activity in a state dependent manner by binding to channels when they are in either the interburst or intraburst closed states. Initial characterization of the inhibitory activity of GaTx1 suggested that the toxin only interacts with CFTR when the channel is in the interburst closed-state, usually thought to represent disruption of the NBD1-NBD2 dimer. These results suggest a substantial change in conformation of the cytoplasmic domains of CFTR during ATP-dependent channel gating. In patches bearing a few CFTR channels, application of GaTx1 or venom resulted in channels that were locked in the interburst closed state for many tens of seconds to minutes (at least 1, 2, or 3 minutes) or causing them to appear to drop out of the record. However, the intraburst inhibition evident in experiments with either Lqh-pf venom or venom fraction C was not present when GaTx1 was used in isolation.

Those skilled in the art will recognize, or be able to ascertain using no more than routine experimentation, many equivalents to the specific embodiments of the invention described herein. Such equivalents are intended to be encompassed by the following claims.

---

We claim:

1. A single polypeptide isolated from scorpion *L. quinquestriatus hebraeus* venom comprising the amino acid sequence of SEQ ID NO:1.

2. The polypeptide of claim 1, wherein the polypeptide binds cystic fibrosis transmembrane conductance regulator.

3. The polypeptide of claim 2, wherein the polypeptide interacts with cystic fibrosis transmembrane conductance regulator in the interburst state.

4. The polypeptide of claim 3, wherein binding of the polypeptide to the cystic fibrosis transmembrane conductance regulator locks closed the cystic fibrosis transmembrane conductance regulator.

5. An isolated synthetic or recombinant polypeptide comprising the amino acid sequence of SEQ ID NO:1.

6. A pharmaceutical composition comprising an effective amount of the polypeptide according to claim 1 or 5 to reduce chloride transport through cystic fibrosis transmembrane conductance regulator and a pharmaceutically acceptable diluent, preservative, solubilizer, emulsifier, adjuvant or carrier.

7. A composition comprising the polypeptide of claim 1 or 5.

8. An ex vivo method of reducing chloride transport through a cystic fibrosis transmembrane conductance regulator (CFTR) channel comprising contacting the CFTR channel with the polypeptide of claim 1 or 5.

9. A method for treating a disorder or symptom of a disorder related to increased cystic fibrosis transmembrane conductance regulator (CFTR) activity comprising:
   administering a therapeutically effective amount of the polypeptide according to claim 1 or 5, wherein the disorder is diarrhea-predominant inflammatory bowel syndrome, autosomal dominant polycystic kidney disease (ADPKD), or secretory diarrhea.

10. An in vivo method of reducing chloride transport through cystic fibrosis transmembrane conductance regulator (CFTR) in a subject having a disorder related to increased CFTR activity, comprising administering to the polypeptide of claim 1 or 5 such that CFTR is contacted with the polypeptide, wherein the disorder is diarrhea-predominant inflammatory bowel syndrome, autosomal dominant polycystic kidney disease (ADPKD), or secretory diarrhea.

* * * * *

UNITED STATES PATENT AND TRADEMARK OFFICE
CERTIFICATE OF CORRECTION

PATENT NO. : 8,106,013 B2
APPLICATION NO. : 12/299881
DATED : January 31, 2012
INVENTOR(S) : Nael McCarty, Matthew Fuller and Julia Kubanek It is certified that error appears in the above-identified patent and that said Letters Patent is hereby corrected as shown below:

Claim 10, column 64, line 16, replace "administering to the polypeptide" with --administering the polypeptide--.

Signed and Sealed this
Twelfth Day of June, 2012

David J. Kappos
*Director of the United States Patent and Trademark Office*